United States Patent
Righini et al.

(10) Patent No.: US 11,123,179 B2
(45) Date of Patent: Sep. 21, 2021

(54) PROSTHETIC DEVICE FOR A HEART VALVE

(71) Applicant: INNOVHEART S.r.l., Milan (IT)

(72) Inventors: Giovanni Righini, Gland (CH); Sarah Zanon, Gland (CH)

(73) Assignee: INNOVHEART S.r.l., Milan (IT)

( * ) Notice: Subject to any disclaimer, the term of this patent is extended or adjusted under 35 U.S.C. 154(b) by 0 days.

(21) Appl. No.: 15/116,586

(22) PCT Filed: Feb. 4, 2015

(86) PCT No.: PCT/IB2015/050849
§ 371 (c)(1),
(2) Date: Aug. 4, 2016

(87) PCT Pub. No.: WO2015/118464
PCT Pub. Date: Aug. 13, 2015

(65) Prior Publication Data
US 2016/0346080 A1     Dec. 1, 2016

(30) Foreign Application Priority Data

Feb. 4, 2014    (IT) .......................... BO2014A000050
Jan. 30, 2015   (IT) .......................... BO2015A000040

(51) Int. Cl.
*A61F 2/24* (2006.01)

(52) U.S. Cl.
CPC .......... *A61F 2/2412* (2013.01); *A61F 2/2409* (2013.01); *A61F 2/2418* (2013.01);
(Continued)

(58) Field of Classification Search
CPC ........ A61F 2/24; A61F 2/2409; A61F 2/2418; A61F 2250/006; A61F 2/2412
See application file for complete search history.

(56) References Cited

U.S. PATENT DOCUMENTS 6,730,121 B2    5/2004    Ortiz et al.
7,648,528 B2    1/2010    Styrc
(Continued)

FOREIGN PATENT DOCUMENTS

FR         2 874 813 A1      3/2006
WO      2008/070797 A2      6/2008
(Continued)

OTHER PUBLICATIONS

International Search Report issued in Application No. PCT/IB2015/050849 in the English language, dated May 28, 2015 (4 pages).
(Continued)

*Primary Examiner* — Christopher D. Prone
(74) *Attorney, Agent, or Firm* — Flynn Thiel, P.C.

(57) ABSTRACT

A prosthetic device for a heart valve, comprising a valve portion with prosthetic leaflets capable of reproducing the function of the valve leaflets of a native heart valve, selectively expandable from a collapsed configuration for implantation to a working expanded configuration. The prosthetic device also comprises a containment portion which surrounds the valve portion to contain its expansion in the working expanded configuration. The prosthetic device also comprises a connecting portion which stably connects the valve portion to the containment portion by means of connecting elements. The invention allows for both the use of minimally invasive surgical implantation procedures and implantation procedures based completely on transcatheteral techniques.

26 Claims, 25 Drawing Sheets

(52) U.S. Cl.
CPC ............ *A61F 2210/0014* (2013.01); *A61F 2220/0033* (2013.01); *A61F 2220/0091* (2013.01); *A61F 2250/006* (2013.01); *A61F 2310/00023* (2013.01)

(56) References Cited

U.S. PATENT DOCUMENTS

| | | |
|---|---|---|
| 2005/0137691 A1 | 6/2005 | Salahieh et al. |
| 2008/0077234 A1 | 3/2008 | Styrc |
| 2008/0077235 A1 | 3/2008 | Kirson |
| 2009/0112309 A1* | 4/2009 | Jaramillo ............ A61F 2/2412 623/1.26 |
| 2011/0218620 A1 | 9/2011 | Meiri et al. |
| 2012/0016464 A1 | 1/2012 | Seguin |
| 2012/0165930 A1 | 6/2012 | Gifford, III et al. |
| 2013/0116779 A1 | 5/2013 | Weber |

FOREIGN PATENT DOCUMENTS

| | | |
|---|---|---|
| WO | WO 2008/103722 A2 | 8/2008 |
| WO | WO 2010/037141 A1 | 4/2010 |
| WO | WO 2011/002996 A2 | 1/2011 |
| WO | WO 2011/069048 A2 | 6/2011 |
| WO | WO 2011/106533 A1 | 9/2011 |
| WO | WO 2011/109813 A2 | 9/2011 |
| WO | WO 2011/137531 A1 | 11/2011 |
| WO | WO 2012/011108 A2 | 1/2012 |
| WO | WO 2012/063228 A1 | 5/2012 |
| WO | WO 2013/096541 A1 | 6/2013 |
| WO | WO 2013/175468 A2 | 11/2013 |

OTHER PUBLICATIONS

Written Opinion of the International Searching Authority issued in Application No. PCT/IB2015/050849 in the English language, dated May 28, 2015 (6 pages).
Written Opinion of the International Preliminary Examining Authority issued in Application No. PCT/IB2015/050849 in the English language, dated Feb. 11, 2016 and reply thereto dated Mar. 30, 2016 (9 pages).
Notification of Transmittal of the International Preliminary Report on Patentability issued in Application No. PCT/IB2015/050849 in the English language, dated Jun. 1, 2016 (1 page).
International Preliminary Report on Patentability issued in Application No. PCT/IB2015/050849 in the English language dated Jun. 1, 2016 (6 pages).
Official Letter of European Patent Office issued in Application No. 15 710 894.5 dated Jul. 2, 2018 (6 pages).
Japanese Office Action issued in corresponding Japanese Patent Application No. 2016-546499, with English translation, dated Aug. 25, 2020 (9 pages).

\* cited by examiner

PROSTHETIC DEVICE FOR A HEART VALVE

FIELD OF APPLICATION

The present invention relates to a prosthetic device for a heart valve. The prosthetic device can be implanted to replace the physiological function of a malfunctioning heart valve. The invention has been developed with particular regard to a prosthetic device for an atrioventricular heart valve.

BACKGROUND OF THE INVENTION

Heart valves are complex and delicate organs which regulate the correct functioning of the human heart. Their main task is to make blood flow within the cardiac cavities unidirectional, which is essential both in the phase of filling the cavities, known as the diastolic phase, and in the blood ejection phase, known as the systolic phase.

To optimise the efficiency of the blood pumping action, the structure of the heart consists of two different compartments, namely the right and left compartments, each of which is in turn subdivided into two chambers, the atrium and the ventricle. The right compartment of the heart, consisting of the right atrium and ventricle receives blood from the peripheral circulation and sends it to the pulmonary circulation to be oxygenated. The left compartment, similarly subdivided into the left atrium and ventricle, supplies the peripheral circulation, receiving the oxygenated blood from the pulmonary circulation and pumping it towards the systemic circulation.

In order to make blood flow within the heart unidirectional, a valve is positioned at the exit of each chamber. The valves sited at the exit of the atria are called atrioventricular, in that they connect the atrial chamber to the ventricular chamber of each side of the heart. In the right side of the heart this valve is also called the tricuspid; in the left side it is only referred to as the mitral valve. Finally, the valve positioned at the exit from the right ventricle is called the pulmonary valve, while the valve at the exit from the left ventricle is called the aortic valve.

Diseases which adversely affect the functioning of a heart valve are among the most serious of the cardiovascular disorders. Of these, the insufficiency of the mitral valve, or its inability to close completely, is a very disabling valve disease because it reduces the efficiency of the pumping action of the left side of the heart, which is responsible for the blood supply of the whole body.

At the current state of the art, the standard therapy for treating severe valve dysfunctions is to replace the valve with an implantable prosthesis. In other cases, mainly in the case of dysfunctions of the mitral valve, it is repaired. In both cases this is achieved via an open heart surgical procedure which provides direct access to the malfunctioning valve. This procedure requires the heart to be stopped temporarily and the creation, using suitable pumps and oxygen exchangers, of an extracorporeal artificial blood circuit. In spite of the refinement of the techniques used to manage the cardiac arrest and the improvement in extracorporeal circulation systems, open heart treatment presents risks due to its invasiveness and the time taken for the procedure. Indeed, implantable prostheses, both for repair and replacement, normally used in traditional surgery usually require a long operation in order to be fixed in the implantation site using specific suturing techniques. Indeed, in a number of cases, it is not possible to perform surgery because of the patient's general condition, for example his advanced age or the presence of concomitant diseases.

In order to overcome these limitations, procedures have been developed recently which are far less invasive, called transcatheteral procedures. For this purpose, radially collapsible and self-anchoring prostheses are used at the implantation site. The prostheses can be implanted by means of catheters able to navigate inside the vascular system and release the prosthetic device reaching the implantation site by remote access performed, for example, in a peripheral vessel, such as a vena cava, the femoral artery, etc. Valve dysfunctions can therefore be corrected with the heart beating and with limited use of surgical practice. To date, transcatheteral techniques are currently only being used clinically for the treatment of the aortic valve.

The situation regarding the treatment of dysfunctions of the atrioventricular valves is different, in particular the treatment of mitral insufficiency. The complex anatomical configuration of the valve and of the structures which surround it, the variability of the diseases, which in turn differ greatly among themselves, which affect the valve directly or indirectly, make it extremely difficult to meet the requirements for a secure and effective implant on the mitral valve via the transcatheteral route.

Even in the variety of the individual designs, the main technologies developed for transcatheteral prostheses for atrioventricular valves differ mainly on the basis of the solution used for the mechanism of anchoring to the implantation site.

A number of known prostheses for atrioventricular valves include devices which are fixed to the implantation site using various types of hooks, stitches, clamps or other mechanical elements capable of hooking up directly with, sometimes even physically penetrating, one or more elements of the valve or of the surrounding anatomical structures, for example the annulus or the leaflets of the valve. Examples of these prostheses are described in applications WO 2010/037141 and WO 2011/002996, in which two circumferential crowns are described, of hooks and loops respectively, which enable hooking onto the annulus of the mitral valve. In WO 2008/103722 a prosthesis is described with stiches and hooks which hook both onto the annulus and onto the leaflets of the native valve.

Other known heart prostheses have a support structure provided, on the edge directed towards the ventricle, of loops designed to employ the native leaflets or their free margins. On the edge facing the atrium there are provided similar loops or a flaring of the support structure, which create an interference on the atrial side of the valve. The prosthesis is therefore fixed to both sides of the native valve. Examples of this anchoring solution are described in WO 2011/106533, WO 2011/069048, WO 2011/137531 and WO 2012/011108.

Other known heart prostheses comprise two separate components which are implanted according to a well-defined sequence. In general, the procedure provides for a first substantially annular component to be implanted separately and independently on the native atrioventricular valve, usually level with the annulus. The second component of the heart prosthesis is implanted after a period of time which can range from a few minutes to several days. The second component comprises the prosthetic functional leaflets and uses the first component as an anchoring element, through direct mechanical coupling, which does not involve the native valve directly. Examples of this design solution are described in U.S. Pat. No. 6,730,121, US 2012/016464, FR 2.874.813, US 2008/077235 and US 2005/137691. Even if the design of the specific embodiments is very different, these patent documents describe solutions which can be brought back to the same anchoring principle.

Other known heart prostheses comprise separate components, separated from one another at the preimplantation stages, but the final anchoring of which necessarily requires the direct involvement of both all the components and of the native valve. One example is described in WO 2011/109813, where a linear element, for example a wire or a band, is released around the mitral valve and then closed again on itself, in order to surround the leaflets of the valve. The linear element acts as a containment ring for a valved component, described generically in WO 2011/109813 as a cylindrical structure equipped with prosthetic functional leaflets, which is expanded inside the native mitral valve. The leaflets of the native valve therefore remain entrapped between the linear element and the valved component, creating, owing to the friction between the various components, the anchorage of the prosthetic system to the implantation site. In WO 2012/063228 another example of a prosthesis comprising an annular element which is deployed to correspond to the native mitral valve is described. The position of this device can be either subannular, in which case the structure is subdivided into several parts so as to have the double open and closed configuration, or supraannular, in which case it is a simpler single structure with a closed configuration. In both, the annular element is positioned so as to entirely surround the leaflets of the native valve near their insertion on the annulus, without, however, anchoring themselves independently. A second implantable element, comprising the prosthetic leaflets, is expanded inside the mitral valve and the first annular element, engaging mechanically with the latter. The solid coupling which results between the various components is able to block the leaflets of the native valve between the two elements, ensuring a reliable and lasting anchorage and effective tightness against reflux.

The above-mentioned known prostheses do not adequately meet a number of essential requirements for the suitable replacement of malfunctioning atrioventricular valves with a transcatheter-type prosthesis. Many of them are not able to ensure contact with the anatomy of the implantation site that is continuous along the whole of the periphery of the prosthesis and stable over time. This requirement is fundamental in order to both obtain secure and balanced anchoring and prevent the possibility of retrograde flow routes being created around the prosthesis.

Another aspect which most of the known prostheses do not take account of is the fact that peripheral tightness against retrograde flow must be obtained without the prosthesis applying a radial force on the annulus of the native valve. Indeed diseases which interfere with the functioning of the atrioventricular valve are often associated with dilatory phenomena sometimes only of the annulus, at other times the heart chambers are involved too. Therefore, a radial force applied to an anatomical structure which already pathologically tends to dilate not only exacerbates the disease itself but provides no guarantee as to the behaviour of the prosthesis in the long-term. The prostheses described in WO 2011/109813 and WO 2012/063228 deal with this aspect, but present the problem of consisting of several components which are independent of one another. This complicates the prosthesis implantation procedure and does not ensure that it is correctly assembled in the final position required for it to function ideally as planned. Furthermore, these prostheses risk being less stable and durable over time.

BRIEF DESCRIPTION OF THE INVENTION

The present invention relates to a prosthetic device for a malfunctioning atrioventricular heart valve, which allows the use of minimally invasive or totally transcatheteral implantation techniques and significantly reduces the times needed for its implantation, solving the problems of the prior art.

The invention is directed at a prosthetic device for a heart valve, comprising:
  a valve portion with prosthetic leaflets capable of reproducing the function of the valve leaflets of a native heart valve, expandable from a collapsed configuration for implantation to a working expanded configuration.
  a containment portion which surrounds the valve portion in order to contain its expansion in the working expanded configuration,
  a connecting portion which connects the valve portion stably to the containment portion.

More specifically, the valve portion comprises a central support element dedicated to supporting all of the prosthetic leaflets, at the same time creating an adequate conduit for blood flow for filling the ventricle. The connecting portion comprises preferably a set of shaped flexible elements which ensure the physical connection and structural union between the central support element and the containment portion. Below these elements of the prosthetic device will be referred to overall as connecting elements.

According to a first aspect, the prosthetic device has a single and continuous structure, but is functionally differentiated, capable of anchoring itself and sealing itself to an atrioventricular valve without exercising any radial force on the latter or on the surrounding anatomical environment. On the contrary, the prosthetic device is suitable for integrating itself intimately with the native valve to the extent that not only does it replace it in the function of making the blood flow unidirectional, but also stabilises its shape and dimensions, preventing successive dilations and prolapses caused by the disease.

The implantation techniques of the prosthetic device described comprise minimally invasive implantation techniques, such as endoscopic or transcatheteral techniques, or more generally implantation techniques allowing the heart to continue beating without the need for extracorporeal circulation. The prosthetic device can also be implanted using surgical techniques with direct access, but with reduced dimensions, to the implantation site.

With specific reference to the endoscopic or transcatheteral and generally minimally invasive implantation procedures, the structure of the present prosthetic device can take up, entirely or in part, a selectively expandable smaller radial space. This feature is obtained by using a material with superelastic properties, or which allows great deformations of any element of the structure while remaining in the elastic field, that is without undergoing permanent distortions. For example, the equiatomic alloy of nickel and titanium, known commercially by the name of Nitinol, has this type of superelastic properties.

According to an aspect of the prosthetic device, the containment portion is positioned on the back of the leaflets of the atrioventricular valve, in order to surround it completely. The expansion of the central support element inside the native valve until it comes into contact with the containment portion therefore achieves the effect of entrapping and blocking the leaflets of the valve securely within the prosthetic structure. If the deployment of the containment portion takes place at immediately subannular level, very close to the annulus, this interaction between the prosthetic device and the native valve provides the anchoring functions at the implantation site and produces the necessary fluid tightness for the correct functioning of the prosthetic device. Furthermore, by immobilising the native leaflets near their line of insertion on the valvular annulus, this also results in stabilising the anatomical structure, preventing the risk of successive pathological dilatations which jeopardise the long-term performance of the prosthetic device, as well as constituting a worsening of the clinical picture of the patient. Since the prosthetic device is in a single body at the time of implantation, the mechanical continuity between the central support element and the containment portion makes their mutual positioning and the method of integrating the prosthetic device with the leaflets of the native valve clear and independent of the operator, or of the implantation procedure.

According to another aspect of the prosthetic device, the containment portion is obtained with a structure having a substantially annular geometry when seen from above, able to continuously surround the entire native valve. The substantially annular geometry can be shaped beforehand according to profiles which best fit the anatomy of the annulus of the atrioventricular valve, for example oval, oblong, bean-shaped, etc. Furthermore, the substantially annular geometry can be two-dimensional, that is flat, or three-dimensional, shaping itself, for example, to the anatomical saddle shape of the native annulus. The geometry creates a continuous coupling with the native valve throughout its peripheral development, in such a way as to provide balanced anchorage and prevent the creation of routes through which the retrograde blood flow can pass.

According to another aspect of the prosthetic device, the containment portion is substantially non-extendable longitudinally, that is in terms of the length of the peripheral extent, although it is deformable to reduce the space it takes up during the implantation procedure. The requirement for a non-extendable structure results from the need to have an effective restraining element for the expansion of the central support element. In this way the radial force exerted by the central element, which is also necessary to make the anchorage to the native leaflets stable, is supported entirely by the containment portion, thereby avoiding any radial stress on the surrounding anatomy. The deformability requirement in terms of shape results from the need for compatibility with minimally invasive implantation procedures, both surgical and, possibly, transcatheteral.

The atrioventricular valves are characterised by a subvalvular apparatus, comprising tendinous cords and papillary muscles, which creates physical continuity between the so-called free margin of the valvular leaflets and the wall of the ventricle. The leaflets of such valves are therefore connected to the ventricular structure on both margins: on the one hand through the annulus, while on the opposite margin, the free margin, through the tendinous cords. According to another aspect of the prosthetic device, the containment portion is assemblable from an open configuration, in such a way that it can be inserted on the back of the leaflets, in the space between the internal wall of the ventricle and the leaflets themselves, to the substantially annular closed configuration. In other words, the containment portion must be able to configure itself in an initial and temporary open geometry to allow for its positioning on the back of the native atrioventricular valve, and a substantially closed working geometry, at the beginning of the actual implantation procedure, suitable for completely surrounding the native valve and providing the desired contrast to the expansion of the central support element.

According to a particular aspect of the prosthetic device, the open configuration of the containment portion can be obtained by severing the annular structure in accordance with a predetermined position.

According to another particular aspect of the prosthetic device, the open configuration of the containment portion can be obtained by subdividing the containment portion into two or more, not necessarily symmetrical, segments or sub-components. The physical continuity of the containment portion can be reconstituted by connecting each segment directly to its adjacent ones, or through the system of connecting elements, for example in the case in which these fix more than one segment at a time to the central element. In this last solution the connecting elements themselves act as a bridge and connection between the various segments of the containment portion.

By way of a practical example, without wishing in any way to limit the general nature of the invention, reference can be made to the implantation of the prosthetic device on the mitral valve. According to a first solution, the containment portion comprises two segments obtained by severing the annular structure in line with the two commissural regions. In this case one segment of the containment portions coincides substantially with the posterior arch of the valve, that is coincides with the line of insertion of the posterior leaflet on the annulus, while the other segment coincides with the anterior arch, that is with the line of insertion of the anterior leaflet on the valvular annulus. It proves to be advantageous, in this configuration, to have the connecting elements close to the median section of each segment. This solution makes positioning of the containment portion to surround the native valve simple. Indeed in the initial phase of the implantation procedure, each segment can be deformed into a configuration occupying little radial space. Then when the device has been introduced inside the ventricle, each segment, still in the space-saving configuration, can easily be inserted on the back of the corresponding valve leaflet and then released, each one independently, possibly maintaining the central support structure in the collapsed configuration. Simple locking mechanisms positioned at the ends of the segments, such as, for example, mechanical fasteners, make it possible to restore a closed structure to the containment portion, which is deformable but non-extendable.

According to another aspect of the prosthetic device, the segments of the containment portion, irrespective of the number and ways in which they are subdivided, are temporarily separable from the rest of the prosthetic structure, in particular from the valve portion equipped with the prosthetic valve leaflets. In this way the segments of the containment portion can be introduced into the ventricular chamber and positioned partly or entirely around the native valve at different times in relation to the central support element. Then the central support structure, together with all the connecting elements, is introduced into the ventricular chamber, close to the implantation site. In this case too, the physical continuity of the containment portion, just like the entire prosthetic structure, can be reconstituted before the implantation procedure, directly connecting each segment to those adjacent to it, or connecting more segments to the same system of connecting elements, or by means of a combination of the two methods.

In order to reduce the risk of damaging the native leaflets in the zone where coupling with the valve prosthesis takes place, all or part of the containment portion can be covered in tissue, of a biological nature, for example animal pericardium, or of an artificial nature, for example tissue made of PET or PTFE, or a polymer material, for example silicones or polyurethanes, or a combination of the two, for example polymer material internally, covered by a film of tissue. The presence of an external covering of tissue of the containment portion, just as of the central support element, also has the further advantage of promoting the endothelialisation of the same by the surrounding cellular structures, increasing the ability of the prosthetic device to integrate with the surrounding physiological environment.

According to another aspect of the prosthetic device, the containment portion described above can, at the same time, prove to be flexible compared with the deformations which occur in the plane identified by the containment portion itself but substantially rigid compared with the direct deformations outside this plane. This property promotes the maintenance of the correct spatial reference between the containment portion and the central support element, thus meaning that they are substantially in contact in line with a predetermined section of the central element, irrespective of the implantation procedure, of the specific anatomy of the patient and of the method of positioning the prosthesis itself. It is therefore possible to shape suitably the coupling region on the central support element in such a way that it can accommodate the geometry of the section of the containment portion appropriately and in an atraumatic manner. For example a suitably shaped groove can be provided or truncated cone-shaped portions can be positioned in the profile of the central element, or small circumferential cushions can be made with additional material, of either a biological nature, such as animal pericardium, or an artificial nature, such as tissues made of PET or PTFE, silicone polymers, etc. By improving the coupling between the support element and the containment portion, or increasing the extension of the contact surface, it is possible to achieve strong anchorage of the native leaflets between the two elements while keeping the pressure applied low. This last aspect significantly reduces the risk of damage and lesions to the native leaflets, which is advantageous for the long-term reliability of the prosthetic device.

According to another aspect, the prosthetic device comprises a mechanism suitable for stably connecting the valve portion comprising the central support element to the containment portion. Indeed the need to position the containment portion separately from the central body of the prosthesis, in order to be able to deploy it completely behind the leaflets of the native atrioventricular valve, involves the presence of a mechanism able to connect the two main portions of the prosthetic device before final implantation. The operation of the locking mechanism of the two portions, that is the restoration of the structural integrity of the prosthesis, takes place using methods compatible with transcatheteral procedures, that is through remote control of the components, in accordance with the current state of the art of interventional techniques. The locking mechanism is based on the use of guidewires to which the structural elements taking part in the connecting mechanism are constrained. In detail, the locking mechanism includes one or more structures belonging to the containment portion and one or more structures belonging to the central valve element. Owing to the action of the guidewires, these structures are aligned and connected to each other in a stable manner, thus restoring the structural unity of the prosthesis.

According to a particular aspect of the invention, the segments in which the containment portion is subdivided are constrained to one or more guidewires through the presence of hollow structures to enable them to pass through. With this solution the same guidewire system previously positioned around the native valve can be used initially to guide the correct positioning of the containment portion on the back of the native valve leaflets and then also to operate the locking mechanism.

According to another particular aspect of the invention, the central support element has, on its periphery, hollow structures suitable for the passage of one or more guidewires, according to configurations which allow stable, mechanical connection with corresponding hollow structures on the containment portion of the prosthetic device.

According to another particular aspect of the invention, each segment of the containment portion has joint mechanisms which allow it to be deformed elastically until it assumes a straight configuration taking up minimum radial space. In this way, the introduction and deployment of the segments of the containment portion at the implant site can take place inside small-diameter catheters, which make the procedure safer and minimally invasive.

BRIEF DESCRIPTION OF THE DRAWINGS

The solution in accordance with one or more embodiments of the invention, as well as subsequent features and relative advantages, will be better understood with reference to the following detailed description, given purely by way of indication and not limitative, to be read together with the attached figures in which, for the sake of simplicity, corresponding elements are indicated with the same or similar references and their explanation is not repeated. To this end it is expressly understood that the figures are not necessarily to scale, with a number of details which may be exaggerated and/or simplified, and which, unless stated otherwise, are simply used to illustrate conceptually the structures and procedures described.

In Particular.

According to different views.

DETAILED DESCRIPTION OF PREFERRED EMBODIMENTS

Figure 1A:
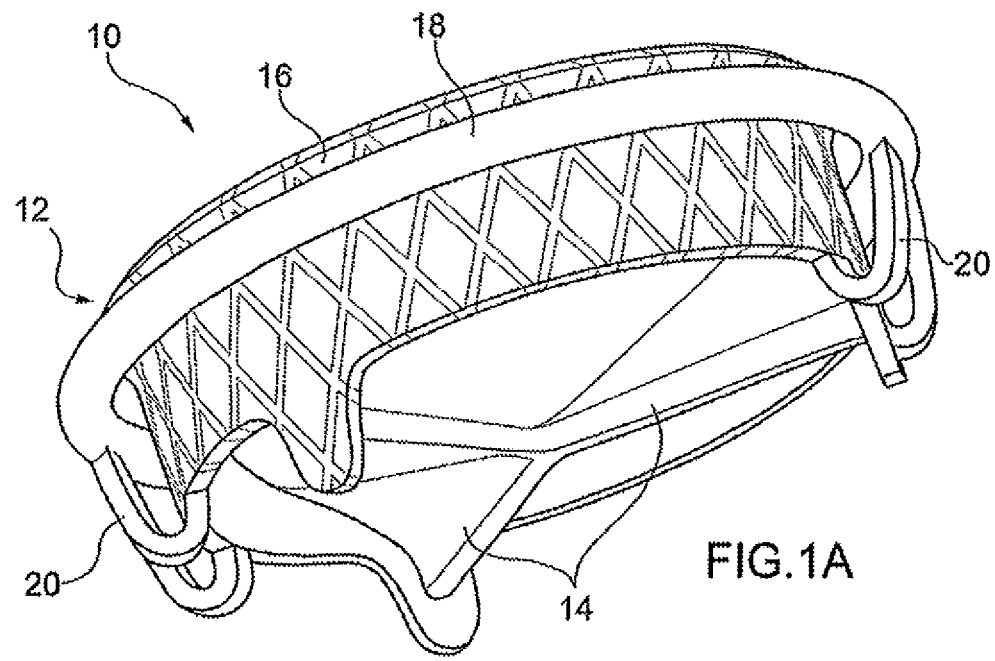
FIG. 1A and FIG. 1B show a general schematic representation of a prosthetic device for the treatment of heart valves, in accordance with an embodiment of the invention.
Figure 1B:
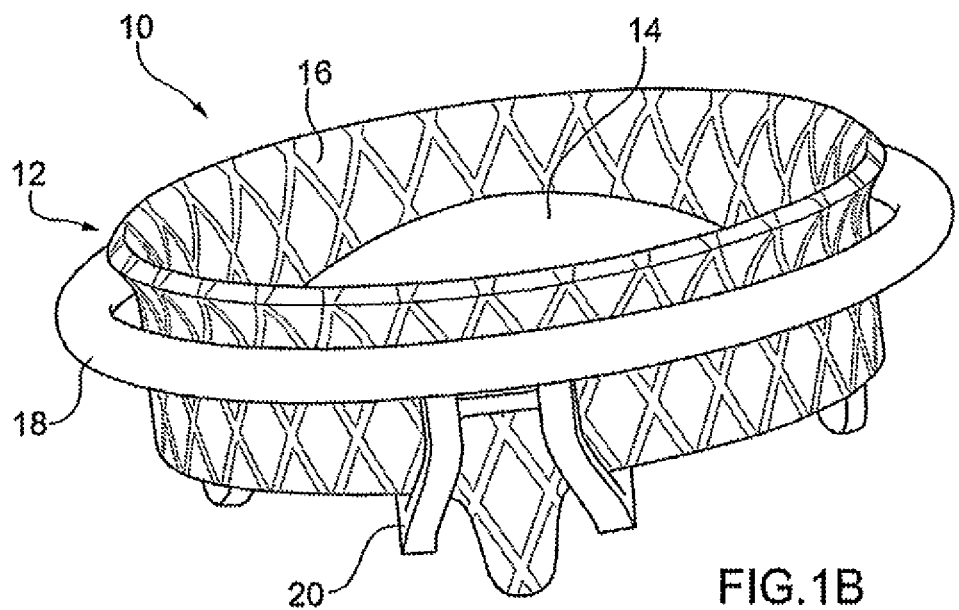

FIG. 1A and FIG. 1B show, according to two different perspectives for a better understanding of the drawing, a general schematic representation of an implantable prosthetic device 10 used to replace the function of an atrioventricular valve, in accordance with an embodiment of the invention.

The prosthetic device 10, as illustrated in FIG. 1A and FIG. 1B, is formed by a prosthetic structure 12 forming a support and interface with the native valve and by a set of flexible prosthetic leaflets 14 fixed to its interior. The prosthetic structure 12 is made in a single body, but three conceptually identifiable portions can be seen therein which are different from one another in functional terms. It is in fact possible to identify:

a central support element 16,
a containment portion 18,
a set of connecting elements 20 for the union of the central support element 16 and of the containment portion 18.

The prosthetic structure 12, just like each of its elements, is designed in such a way as to be collapsible without repercussions on the safety and functionality of the prosthetic device. It is therefore possible to temporarily reduce the radial size of the prosthesis, in order to allow it to be introduced into the cardiac cavities through small aperture access ports, compatible with the techniques of minimally invasive surgery, or even with the known transcatheteral techniques for positioning and implanting cardiac prostheses. In other words it is possible to insert the prosthetic device 10 inside a catheter with a small radial profile, capable of conveying the prosthesis inside the cardiac cavity, close to the implantation site, through direct minimally invasive access routes, for example transapically, or via the transluminal route, and effect its deployment and implantation there, functionally replacing the native valve.

Below is a detailed description of the various portions which make up the prosthetic structure.

The central support element 16 is the portion of the prosthetic structure which delimits the conduit for the passage of blood through the device. Inside the central support element 16 are fixed the flexible prosthetic leaflets which make the blood flow within the conduit unidirectional. Each prosthetic leaflet 14 does in fact have a sealed edge on the internal surface of the central support element 16, while the opposite edge is free to arrange itself according to the flow pattern inside the prosthetic device 10. Under direct flow conditions, and therefore in the open valve configuration, the prosthetic leaflet 14 flexes substantially in the direction of the flow, with the free edge moving away from the axis of the central support element 16, minimising the obstruction to the flow. By contrast, in the closed valve configuration, the prosthetic leaflet 14 positions itself transversally to the direction of the flow, with the free edge of each prosthetic leaflet 14 in contact with the free edge of the contiguous prosthetic leaflets, to entirely occlude the orifice of the conduit. In this way the main function of the valve is activated, that is to make the flow within it unidirectional, preventing the reverse flow and minimising the interference with the direct flow.

In the embodiment illustrated in FIG. 1A and FIG. 1B there are three prosthetic valve leaflets 14, three being the optimum number of leaflets in a cylindrical orifice. Nevertheless the functioning principle does not change substantially even if there is a lower number of leaflets, for example two, or a number higher than three. The central support element 16 is a radially collapsible elastic structure, which tends, due to its elastic recovery, to expand even to a diameter higher than the maximum diameter which maintains the coaptation, that is the contact, between the free margins of the closed prosthetic leaflets 14.

The containment portion 18 is the portion of the prosthetic structure which contrasts and limits the free expansion of the central support element 16, preventing it from exceeding the maximum diameter compatible with the preservation of the coaptation between the prosthetic leaflets 14. The containment portion 18 has a substantially annular geometry and is longitudinally non-extendable, that is it does not significantly change its peripheral extent even when the central support element 16 expands inside it, applying a radial force to the outside. During the implantation procedure, when the prosthetic device 10 is positioned for the final release in line with the implantation site, the containment portion 18 is disposed outside of the native atrioventricular valve, surrounding the valve leaflets completely, while the central support element 16 is inside the native valve leaflets, substantially on the axis of the orifice of the atrioventricular valve. Following the final release, the central support element 16 expands until it meets the containment portion 18, with which it couples on the external surface. As a consequence of the design of the prosthetic structure, the leaflets of the native valve remain entrapped inside the coupling between the two portions of the prosthetic device 10. Furthermore, the containment portion 18 also has the function of stabilising the native valvular annulus, preventing the radial force exerted by the central support element 16, although necessary to guarantee effective anchorage of the prosthesis, from being transferred to the surrounding anatomical structure, which is usually affected by degenerative and dilatory processes associated with the disease which makes the atrioventricular valve malfunction.

Finally, the set of connecting elements 20 is that portion of the prosthetic structure 12 which physically links the central support element 16 and the containment portion 18, making the prosthetic structure 12 a single and continuous entity. The monolithic structure allows for safer and effective functioning of the prosthesis, making the anchorage mechanism of the prosthesis stable and durable, as well as simplifying and accelerating the implantation procedure, with immediate and reproducible positioning of the prosthesis, as can be seen from the practical examples described in the following figures.

In order to make the explanations clearer, in the outlines of FIGS. 1A and 1B, as well as in the figures which will follow, the external diameter of the central support element 16 is shown with smaller dimensions than the internal dimensions of the containment portion 18. In other words the figures show these two components of the prosthetic structure not in contact with each other in the fully expanded configuration. It is possible to have over-sizing of the central support element 16 compared with the dimensions of the containment portion 18. In this case there is interference between the two portions of the prosthetic structure 12 and in fact the central support element 16 applies radial pressure on the containment portion 18 when the latter exerts its expansion-restraining action, irrespective of the thickness of the tissue which remains entrapped between the two portions of the prosthetic structure 12. This radial pressure increases the stability of anchorage to the native valve leaflets.

In order to better illustrate the embodiment of the invention described in FIG. 1A and FIG. 1B, a practical example of this is described below as a prosthesis to replace the mitral valve, the heart valve being positioned between the left atrium and the left ventricle. To this end the anatomical section diagram of the left side of the heart is given in FIG. 2. In it is shown a section in longitudinal axis of the left side of the heart, as it would appear if the posterior wall of the ventricle and of the left atrium had been removed. It is therefore possible to visualise the mitral valve in the projection from the posterior arch, with the posterior leaflet in the foreground and the anterior leaflet on the opposite side to the orifice. The line of insertion of the leaflets on the plane of the valve identifies the annulus of the mitral valve. The zones of the annulus passing between the anterior and the posterior leaflet are indicated as commissural zones. The anatomical section chosen also clearly shows the sub-valvular apparatus, consisting of tendinous cords and papillary muscles. This subvalvular apparatus creates continuity between the free margins of the valve leaflets and the walls of the ventricle.

Figure 2:
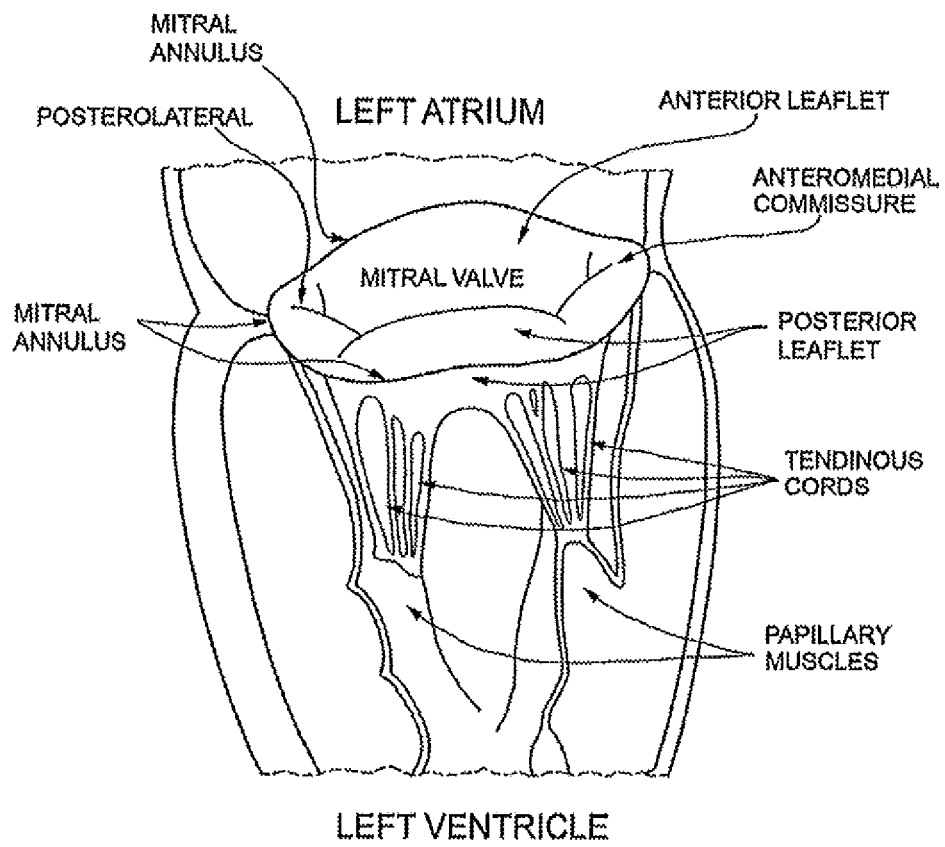
FIG. 2 is a sectional view of the left side of the heart, with particular attention to the anatomy of the atrioventricular valve. This view will be used to illustrate specific applications of the prosthetic device according to various embodiments of the invention.
Figure 3:
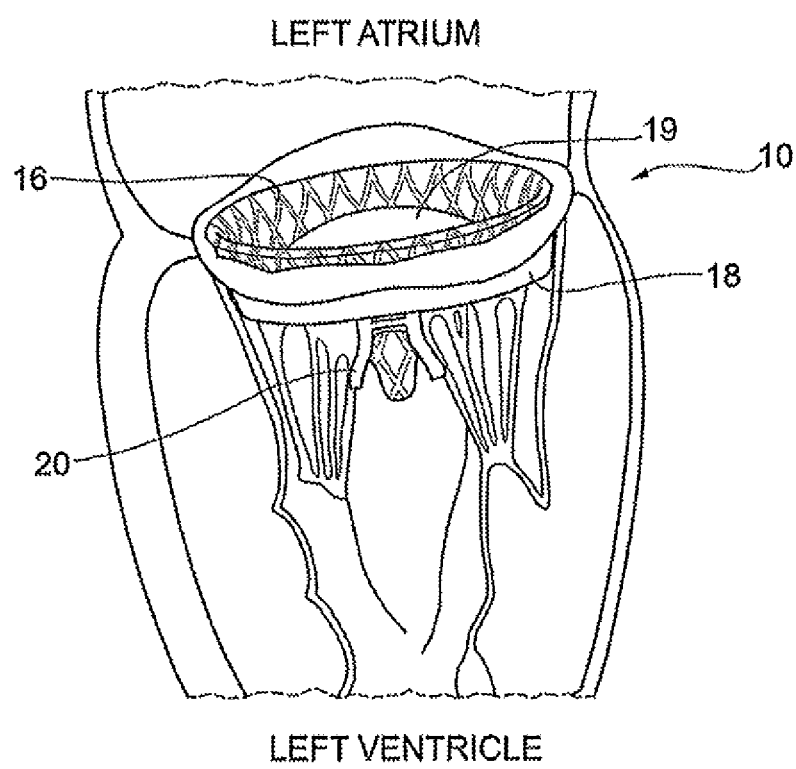
FIG. 3 shows an example of the application of the prosthetic device for the replacement of the atrioventricular valve of the left side of the heart.

FIG. 3 shows an example of the application of the prosthetic device 10 described in FIG. 1, in accordance with a specific embodiment of the invention. The illustrative diagram shown in FIG. 3 shows the central support element 16 of the device expanded inside the mitral valve to create the intraprosthetic passage for the blood flow. The prosthetic leaflets 14 are inside this passage, with the function of making the flow unidirectional. While the central support element 16 is inside the native mitral valve, the containment portion 18 of the prosthesis is positioned on the back of the native leaflets, to surround the mitral valve externally, as a limitative restraint on the expansion of the central support element 16. It is clear how the design of the prosthetic structure 12 is such that the implanted prosthesis does not apply any stress to the mitral annulus. The two groups of connecting elements 20 of the prosthetic structure pass over the mitral valve in the subvalvular space close to the midline of each native leaflet, avoiding any interference with the bundles of tendinous cords which tend to open out in such regions. Because of the specific anatomical view, FIG. 3 shows only one of the groups of connecting arms 20, namely the one which passes over the posterior leaflet. A similar arrangement is also created symmetrically on the median portion of the anterior leaflet, remaining hidden in the perspective in FIG. 3. It should be noted that, anatomically, on the median portion of each valve leaflet an aperture is effectively created in the bundles of tendinous cords which depart from the free margins, as shown in FIG. 2 for the posterior leaflet. Each valve leaflet is in fact connected, by the tendinous cords, to both of the papillary muscles, which are found in positions almost opposite the ventricular cavity. This aperture in the combs of the tendinous cords constitutes an excellent passage for the connecting elements 20 of the prosthetic structure.

From FIG. 3 it is also clear how the connecting elements 20 contribute to the anchoring of the prosthesis, above all during the critical systolic phase, when the atrioventricular valve is closed and the ventricular pressure, at its maximum, pushes the prosthesis towards the atrium. It is in fact clear how the connecting elements 20, being one with the containment portion 18 segregated on the back of the native leaflets, operate as one structure which securely fastens the central support element 16 to the annulus of the valve, effectively integrating the anchoring action due to the capture and trapping of the native leaflets inside the prosthetic structure itself.

Figure 4:
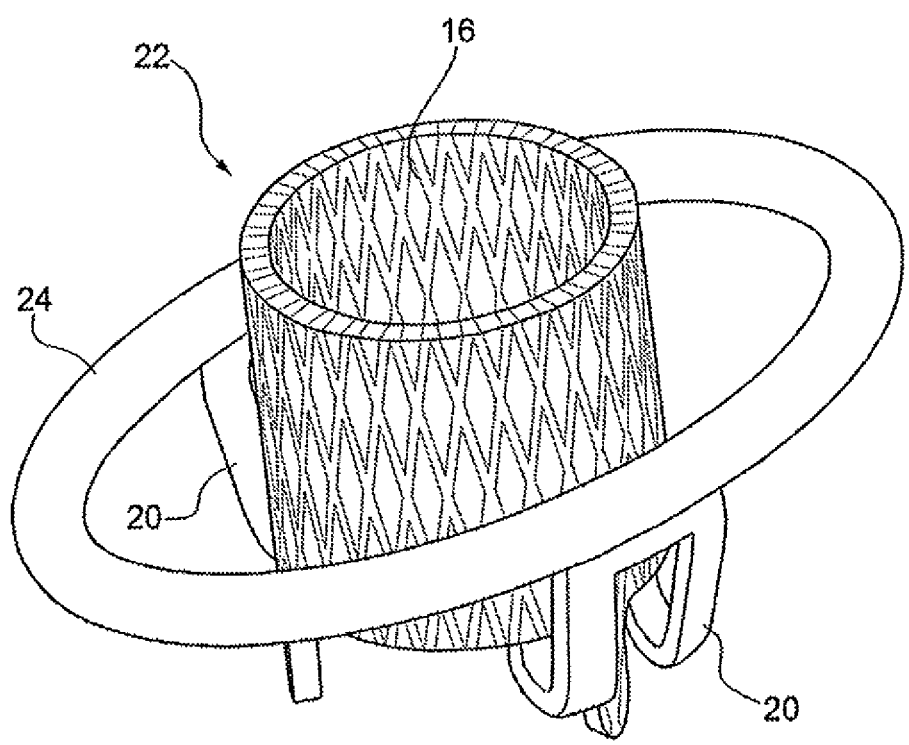
FIG. 4 shows a different embodiment of the prosthetic device for the treatment of heart valves, characterised by an oblong geometry of the containment portion.

FIG. 4 shows another version of the prosthetic structure 22, in accordance with a different embodiment of the invention. In this embodiment the containment portion 24 of the prosthetic structure maintains an annular and non-extendable form, but has an elongated oval geometry on one axis, an alternative to the substantially circular geometry of the containment portion 18 described in FIG. 1. To simplify the diagram, the prosthetic valve leaflets are not shown, being superfluous for the purposes of the description, and furthermore the central support element 16 is shown in a compressed configuration, as an example of the geometry assumed during the implantation procedure before the final release.

It should be noted, with reference to the configuration shown in FIG. 4, how appropriate it is to provide the connecting elements 20 with arms, the cross section of which has a relatively small thickness (by way of indication and not limited to the range of from 0.25 mm to 0.75 mm) and a significantly larger transverse dimension (for example, still not limitatively, in the range of from 0.5 m to 3 mm). Owing to this sizing, and to the particular design with loops, the connecting elements 20 prove to be flexible radially, but rigid if loaded tangentially or axiallyx. They are therefore suitable for compensating for any variation in the radial distance which is created between the containment portion 24 (or 18) and the central support element 16, for example when the first is deployed while the latter is still in a compressed configuration as shown in FIG. 4. At the same time, however, they are suitable for keeping clear the reference between the two elements during the implantation procedure, avoiding, for example, a dislocation of the containment component in respect of the central element during the positioning of the prosthesis in contact with the annulus of the mitral valve.

The containment portion 24 having an elongated, oval or bean-shaped, symmetrical or asymmetrical shape, is often more suitable for coupling itself to the anatomical shape of the annulus of the atrioventricular valve, even in the presence of pathological conditions. Indeed during the first phases of the implantation procedure the containment portion 24 of the prosthetic device, already deployed in the ventricular chamber, has to fit substantially with the ventricular aspect of the annulus of the native valve. Indeed positioning the containment portion 24 in close proximity to the line of insertion of the valve leaflets in the annulus ensures both the life of the anchorage, being the thickest and most robust zone of the leaflet, and the complete tightness to counter flow, in that there is continuity of the leaflets along the entire periphery of the valve. As regards this last point, account has to be taken of the fact that the extension of the valve leaflets reduces significantly in the commissural zones, where there is the transition between the two leaflets of the valve. Therefore, if the prosthesis is placed in too low a position in the ventricle, this increases the risk that the continuity of the leaflets entrapped inside the coupling between the containment portion and the central element will be interrupted at the level of the commissural areas, thus limiting itself to the principal arches.

This lack of continuity in the sealing ring creates leaks outside the prosthetic conduit, and therefore a loss of tightness of the prosthesis to reverse flow. Choosing the geometry of the annular portion of the prosthesis, according to the anatomy and the pathology to be treated, makes for easier and more effective positioning of the structure itself close to the native annulus, on the back of the native leaflets, positioning facilitated by the geometrical correspondence of the parts. On the basis of simple pathophysiological considerations known at the state of the art, the optimum geometry of the annular portion can be selected both two-dimensionally and three-dimensionally, for example according to a saddle shape in the space.

It is useful to point out that the geometry adopted by the annular portion during the initial phase of coupling with the native valvular annulus may not affect the final geometry of the expanded prosthetic structure, in particular the shape of the prosthetic orifice, which ensures the best operating conditions for the prosthetic leaflets. It is indeed possible, in accordance with the various embodiments of the invention, to vary, with a considerable degree of freedom, the rigidity to flexion of the containment portion, also creating cross sections with anisotropic elastic characteristics, while still meeting the essential requirement of longitudinal non-extendibility of the portion itself. It is possible to design the annular portion in such a way that it is substantially flexible according to deformations which remain on the plane identified by the element itself, while being substantially rigid for all the direct deformations outside this plane. With a design of this kind the containment portion cannot be deformed, in the direction of the axis of the prosthesis, during the positioning of the device in the best position for implantation, preventing it from being misaligned with respect to the coupling region on the external surface of the central support element. At the same time its deformability on the plane allows it to adapt itself perfectly to the expanded geometry of the central support element, thus promoting continuous coupling between the two structures without, moreover, interfering with the correct functioning of the prosthetic leaflets, which requires a pre-defined working geometry of the support element which contains them. As an example of that described above, it is therefore possible to design the containment portion with any oblong geometry suitable for coupling with the native annulus at the time when it is positioned in the subannular groove of the native valve, keeping said containment portion planar during all the positioning phases, owing to its rigidity to deformations outside the plane, and ultimately, when it is implanted, to make it conform to the final cylindrical geometry of the support element, owing to its deformability in the plane.

Figure 5A:
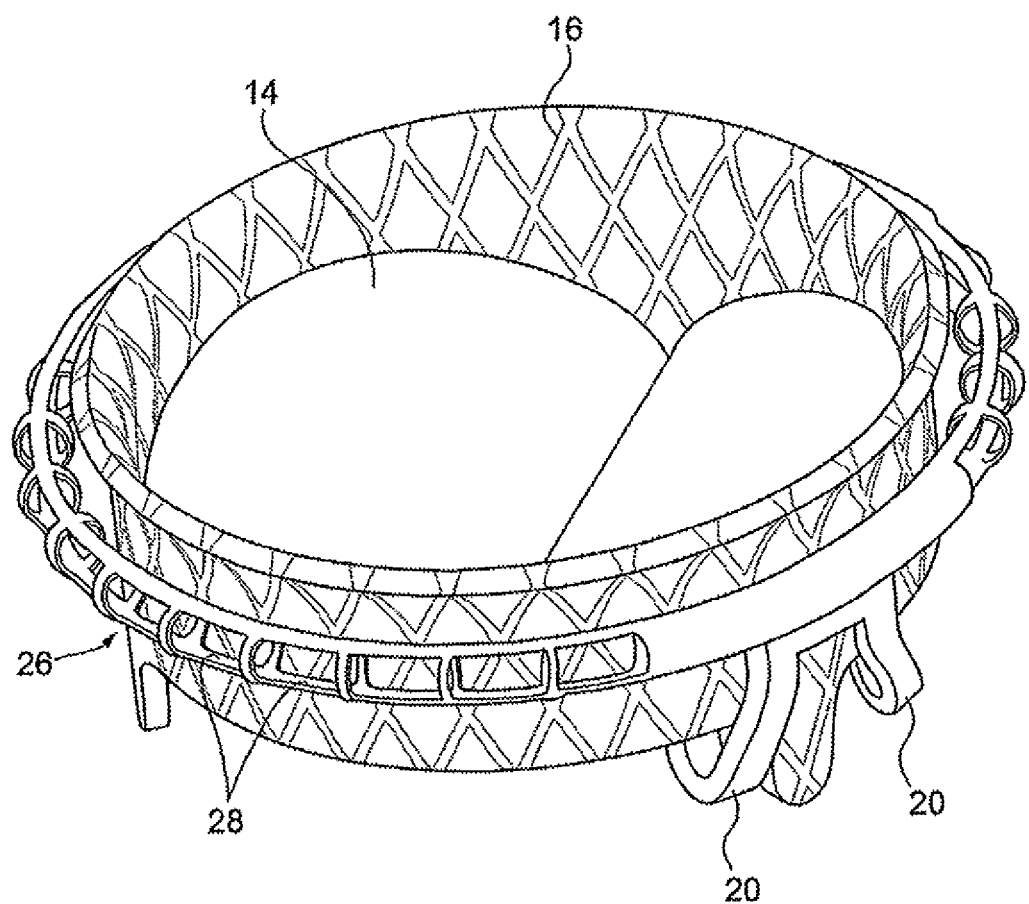
FIG. 5A and FIG. 5B show a different embodiment of the containment portion of the prosthetic structure, in accordance with an embodiment of the invention.
Figure 5B:
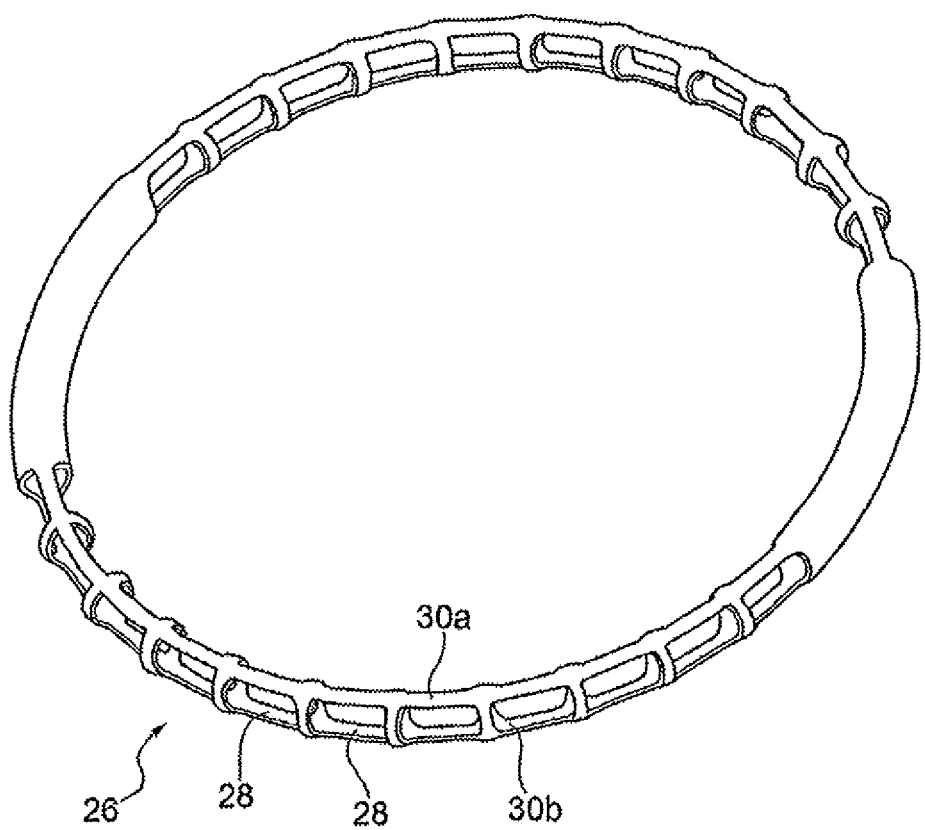

Purely by way of example, without limiting the general nature of the invention, an embodiment of a containment portion 26 which satisfies the characteristics of an anisotropic elastic response described above is shown in FIG. 5A, as an integral part of the prosthetic structure, and in FIG. 5B, where it is shown in isolated form, for greater clarity. The containment portion 26 is formed by a substantially tubular structure, the flexibility of which is regulated by a series of openings 28 having selected dimensions and position. In the example shown in FIGS. 5A and 5B, the openings 28 are aligned along two principal generators, one on the internal face and one on the external face of the containment portion 26. This creates two continuous bands 30*a*, 30*b*, one on the upper side and one on the lower side, which make the annular portion particularly rigid to deformations outside the plane. This rigidity is in accordance with the width of the band. The dimensions of the single opening and the distance between adjacent openings, on the other hand, determine the elastic characteristics to flexion in the plane.

Figure 6:
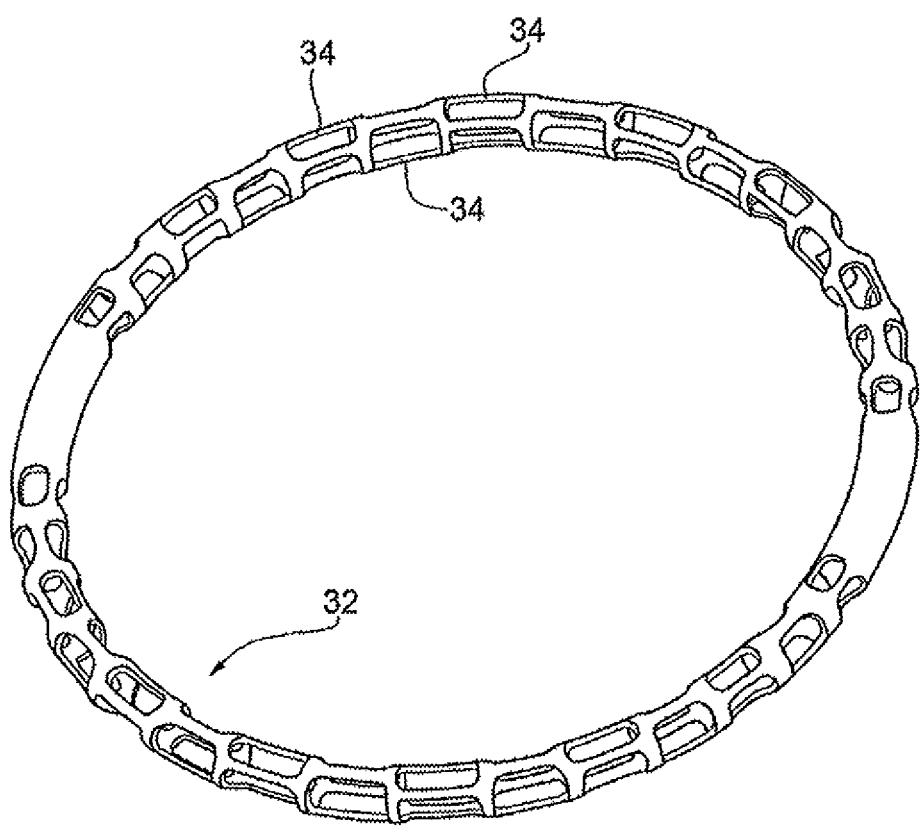
FIG. 6 shows a subsequent embodiment of the containment portion of the prosthetic structure, in accordance with an embodiment of the invention.

Another example of an embodiment of a containment portion 32 is described in FIG. 6. This figure also shows the containment portion 32 isolated from the rest of the prosthetic structure, for greater clarity. In this example, which does not limit the general nature of the invention, the containment portion 32 is in tubular form with openings 34 positioned according to a cyclical sequence which reduces the anisotropy of the elastic response of the annular portion, resulting in the openings being more uniformly distributed on the surface. With this geometry too it is possible to modulate the elastic response according to the direction of the flexion. For example, by reducing the size of the openings 34 positioned on the upper and lower sides compared with the dimensions of the openings 34 positioned on the internal and external sides of the containment portion 32, greater rigidity to deformations outside the plane is achieved compared with the deformations coplanar to the structure. Still by way of example, without wishing to limit the general nature of the invention, FIG. 6 also shows the modulation of the size of the openings 34 according to their angular position on the annular portion, in order to obtain a structure having elastic properties which vary along the periphery according to predetermined requirements. With the geometry shown in FIG. 6, for example, there is a containment portion 32 the flexional pliability of which, while still being anisotropic in each cross section, increases by distancing itself from the portions of continuity with the connecting elements 20 until it is at its maximum close to the median region.

The embodiments shown in FIG. 5 and FIG. 6 refer conceptually to the structural component of the containment portion. To reduce the risk of lesions to the anatomical structures of the implantation site, such a structural component can be covered with polymer material, for example silicone or polyurethane, and/or tissue, in order to recreate a continuous and atraumatic external surface. The use of tissue, both artificial and biological, for the external surface of the containment component also increases its aptitude to be endothelialised and therefore physiologically integrated at the implantation site.

As described previously, the sub-valvular structure of the atrioventricular valves creates anatomical and functional continuity between the heart valve and the ventricle wall. Each valve leaflet is therefore continuous with the cardiac structure on the one hand through the annulus and on the other through the tendinous cords and papillary muscles. This continuity is important for the stability of the ventricular chamber and it is desirable for the treatment of the valve dysfunction to avoid any interference therewith. Because of this constraint, the requirement to surround the atrioventricular valve externally with the containment portion of the prosthetic structure may be satisfied by providing it with a transitory open configuration, such as to allow it to be positioned in the space between the back of the native leaflets and the ventricle wall, without the need to interrupt the continuity between the ventricle and the valve. The subsequent requirements of flexional pliability and longitudinal non-extendibility of the containment portion suggest that the open configuration represents a temporary condition associated with its preimplantation positioning behind the native valve, while for the actual implantation phase and under operating conditions the containment portion has a closed and substantially continuous configuration.

Figure 7:
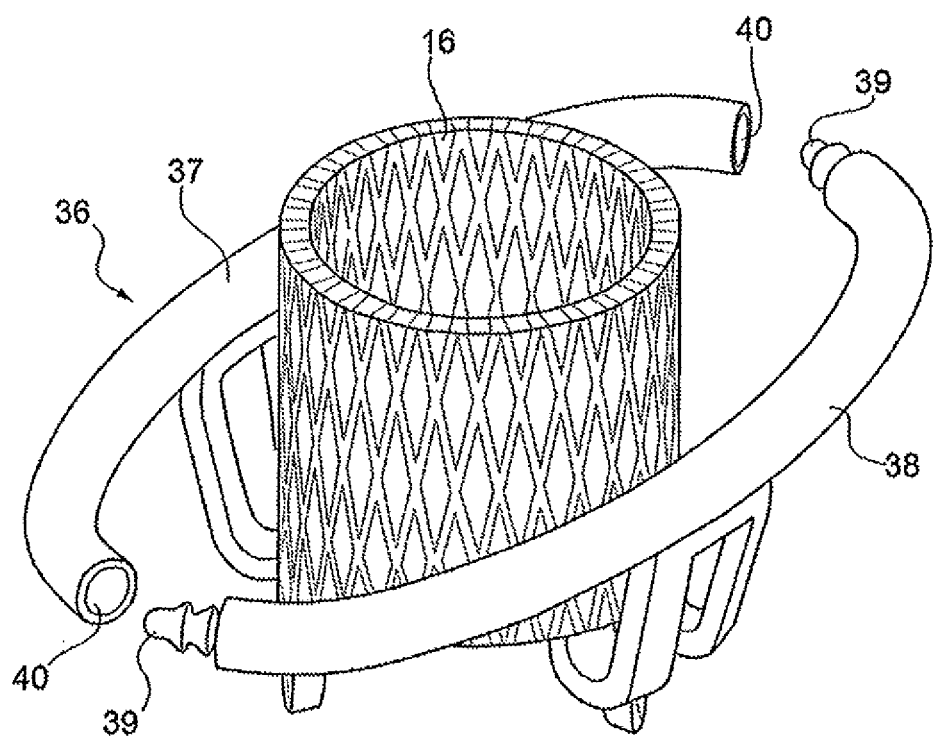
FIG. 7 shows an example of a prosthetic device for the treatment of heart valves, in accordance with an embodiment of the invention, characterised by having the containment portion of the prosthetic structure embodied in such a way as to present two separate configurations: an open, temporary, configuration, and a closed configuration, which corresponds to the working configuration.

FIG. 7 shows a version of the prosthetic structure, in accordance with various embodiments of the invention, which provides for a containment portion 36 having a configuration which can go from temporarily open to closed. In the example given in the figure, which does not limit the general nature of the invention, the containment portion 36 is separated into two curved segments 37, 38, each segment 37, 38 being equipped with a mechanism for the reclosing of the annular geometry in a phase subsequent to its positioning on the back of the native valve leaflets. In the example shown, this mechanism comprises a shaped pin 39, for example with a saw tooth, facing a cavity 40 having the design and dimensions to prevent the coming out of the shaped pin 39 once this has been inserted into cavity 40. The cavity 40 can be designed in such a way as to be radially elastic. In this way it is possible to have slight interference between the shaped pin 39 and the cavity 40, increasing the solidity and reliability of the closure mechanism. Obviously the closure mechanism can take equivalent alternative shapes. For example the cavity 40 can itself have a sawtooth profile internally, produced by elastic lamellae (not illustrated) which protrude into the cavity 40. In general, the use of super-elastic material for creating the prosthetic structure makes it easier to create deformable structures which improve the effectiveness of the coupling.

Figure 8A:
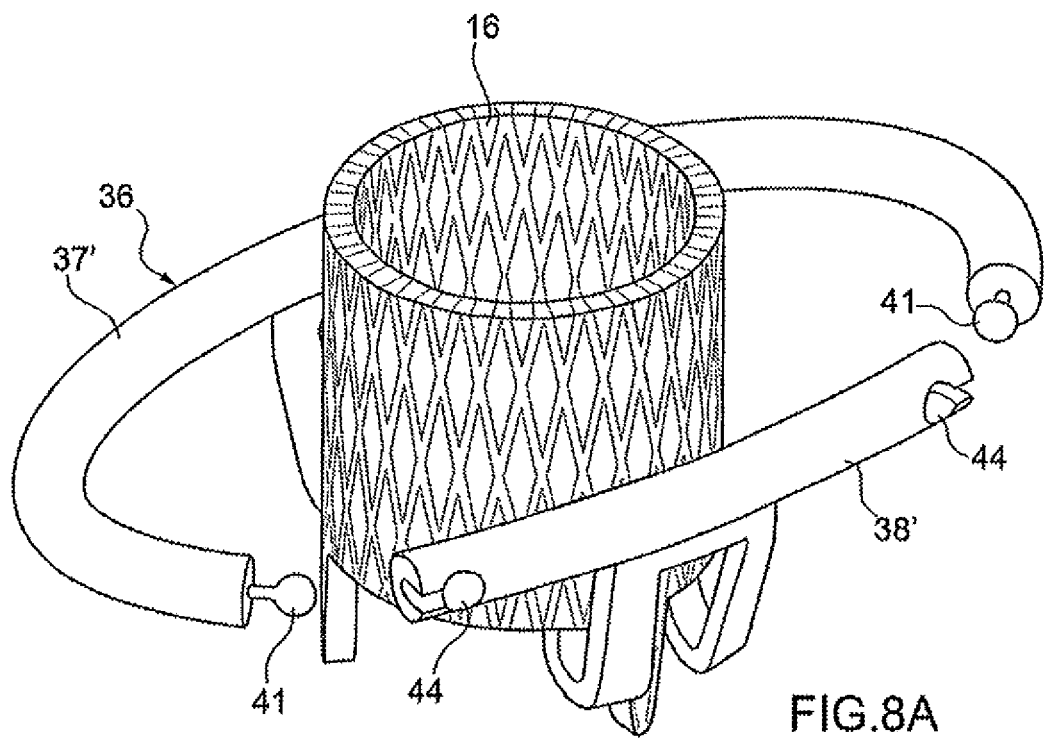
FIG. 8A and FIG. 8B show a different embodiment of a prosthetic device for the treatment of heart valves, in accordance with an embodiment of the invention, characterised by a different configuration of the containment portion of the prosthetic structure.
Figure 8B:
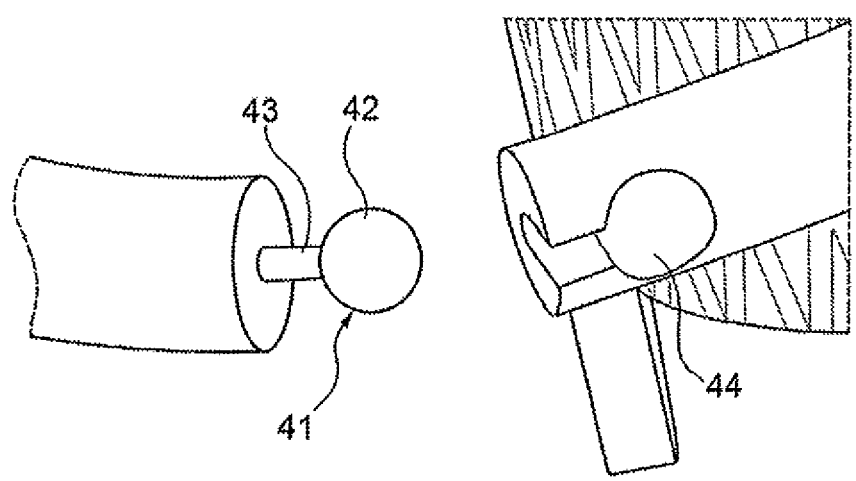

FIG. 8A and FIG. 8B show another version of the prosthetic structure, which is again in accordance with various embodiments of the invention. The solution described in FIG. 8A has a geometry that may prove to be particularly advantageous for implantation on the mitral valve. In this version the sub-division of the containment portion 36 is made asymmetrically, replicating, for example, the anatomy of the native valve, where the posterior annular arch 37', that is the one on which the posterior leaflet rests, is longer than the anterior annular arch 38', on which the anterior leaflet rests. In this case, once inserted onto the back of the posterior leaflet, the longer segment surrounds the commissural regions with the terminal portions of this segment, shaped with a suitable curvature, the closure mechanisms of both sides are positioned in the subaortic space of the ventricle, known as the LVOT (left ventricle outflow tract). In this region of the ventricle, which is substantially free from the elements of the mitral sub-valvular apparatus, it may be simpler to trigger the reclosure mechanism of the containment portion, directly in the case of an open-heart surgical procedure, using interventional techniques during a transcatheteral procedure. FIG. 8A also shows an alternative design for the closure mechanism, given in greater detail in FIG. 8B. In this design, the ends of a segment are equipped with a shaped element 41 which protrudes axially. In the example in FIG. 8B, although this does not limit the general nature of the invention, this shaped element 41 has the shape of a sphere 42 connected to the end of the segment by a pin 43 of a smaller diameter than the sphere 42. On a lateral portion of the corresponding end of the other segment there is a blind cavity 44 which reproduces, in negative form, the shaping described previously and which is therefore suitable for accommodating and locking the shaped element 41. The position of this blind cavity 44, on the external face of the segment, means that the radial force exerted on the containment portion 36 by the central support element 16, following its expansion, contributes to the stability of the coupling, preventing the shaped element 41 from coming out of the corresponding cavity 44 in which it is accommodated.

It should be noted that the flexibility of the segments of the containment portion facilitates their positioning on the back of the native leaflets. It is indeed possible to considerably amplify the apertures present between the segments of the containment portion, compared with that indicated in FIG. 7 and FIG. 8 purely by way of example, in order to surround the native valve with all the segments.

Figure 9A:
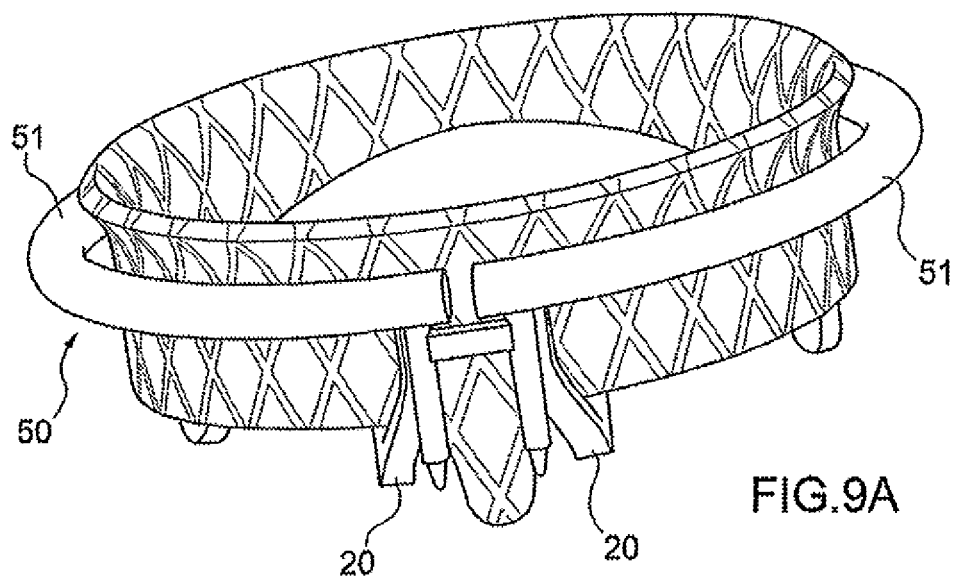
FIG. 9A and FIG. 9B show, according to different views, a general schematic representation of a prosthetic device for the treatment of heart valves, in accordance with an embodiment of the invention, characterised by having one or more parts of the containment portion of the prosthetic structure which are temporarily separable from the remaining portion of the prosthetic structure, it being necessary, however, to reinstate the single body of the structure before implantation of the device.
Figure 9B:
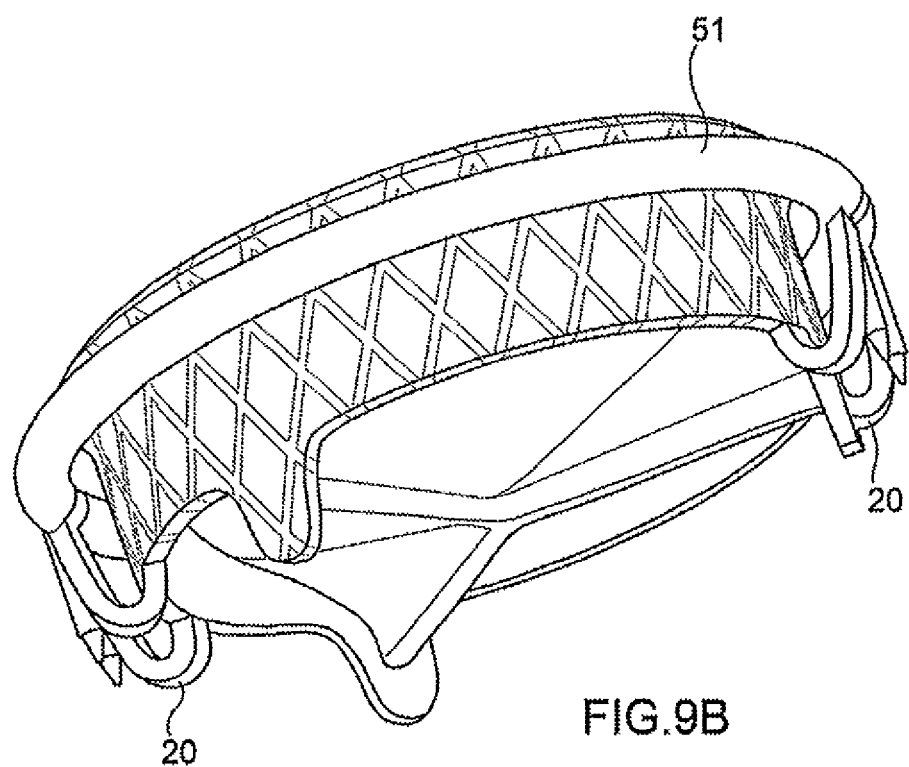

In FIG. 9A and FIG. 9B a different embodiment is described for the implantable prosthetic device, developed for replacing the function of the atrioventricular valve, in accordance with an embodiment of the invention. In this embodiment the containment portion 50, which may have any of the previously described two-dimensional or three-dimensional subcomponents 51 which are separated from one another and obtained by severing the containment portion in line with the connecting elements 20. In addition, each subcomponent is temporarily separable, using any embodiment of a reversible locking mechanism, from those connecting elements to which, however, it is engaged in the final configuration of the implant.

The subdivision of the containment portion into two or more subcomponents combined with the possibility of releasing one or more of said subcomponents from the connecting elements on the central support structure make immediate positioning of the containment portion on the back of the native valve leaflets possible during the first phases of the implantation procedure. Then the restoration of the unity of the prosthetic structure, with the recovery of all functional properties, allows final implantation. The structural continuity of the containment portion, which also ensures the longitudinal non-extendibility of the same and its ability to contrast and limit the radial expansion of the central body, can therefore also be obtained with the contribution of the connecting elements present in the prosthetic structure.

Purely by way of example, without limiting the general nature of the invention, an embodiment of the implantable prosthetic device according to the embodiment described above is illustrated in detail in FIG. 10A to FIG. 10C.

Figure 10A:
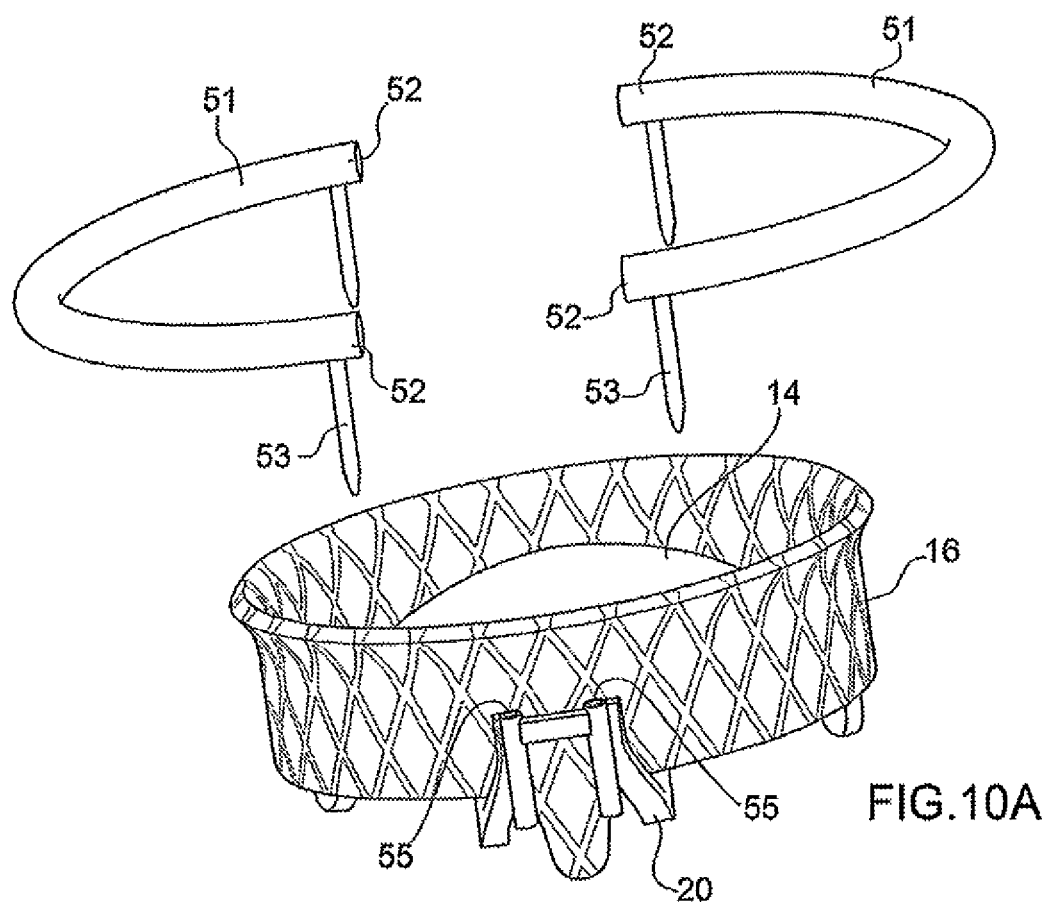
FIG. 10A to FIG. 10C show an example of an embodiment of a prosthetic device for the treatment of heart valves, in accordance with an embodiment of the invention, characterised by having the containment portion of the prosthetic structure subdivided into two parts which are temporarily separable from the remaining portion of the prosthetic structure.

FIG. 10A shows the containment portion 50, of a substantially circular shape for simplicity of representation, subdivided into two subcomponents 51, which are not necessarily symmetrical. The continuity of the containment portion 50 is interrupted in line with the connecting elements 20 to the central support element 16. Each end 52 of each subcomponent 51 is equipped with a pin 53 preferably orientated outside the annular plane. FIG. 10A shows an embodiment in which the pin is orientated substantially perpendicularly to the plane of the annulus. In turn, the connecting elements 20 are equipped with cylindrical cavities 55 each suitable for accommodating each of these pins. A couple of cylindrical seats 55 is present on each of the two groups of connecting elements 22, substantially arranged in angular positions diametrically opposed to the central support element 16. These cylindrical cavities 55, like the pins 53 present at the ends of the segments 51 of the containment portion 50, can be provided with lamellae, teeth or other surface discontinuities intended to increase the friction in the pin-hole coupling, improving the stability of the connection between the subcomponents 51 of the containment portion 50 and the connecting elements 20. The cylindrical seats 55 are orientated in a coherent way to the orientation of the pins 53 present on the subcomponents 51 of the containment portion 50, in such a way that the pin-hole coupling maintains said portion on a geometrically consistent plane with the annulus of the native valve.

Figure 10B:
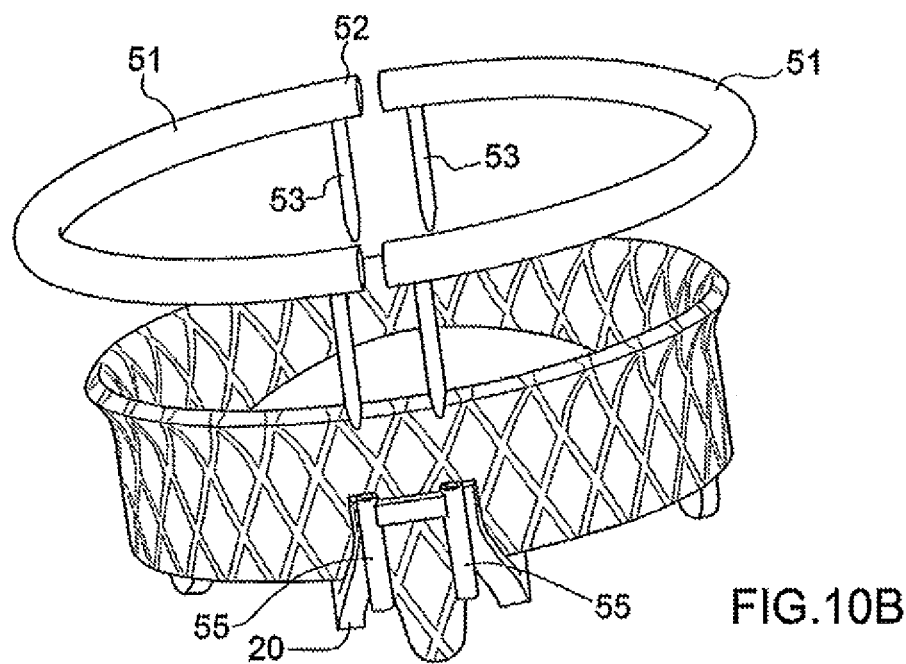

FIG. 10B shows how, once positioned on the back of the native leaflets, the subcomponents 51 of the containment portion 50 can be brought back towards the central element 16 of the prosthetic structure, in such a way that each pin 53 may be substantially aligned with the corresponding cylindrical cavity 55 present on the connecting elements 20 between the two portions.

Figure 10C:
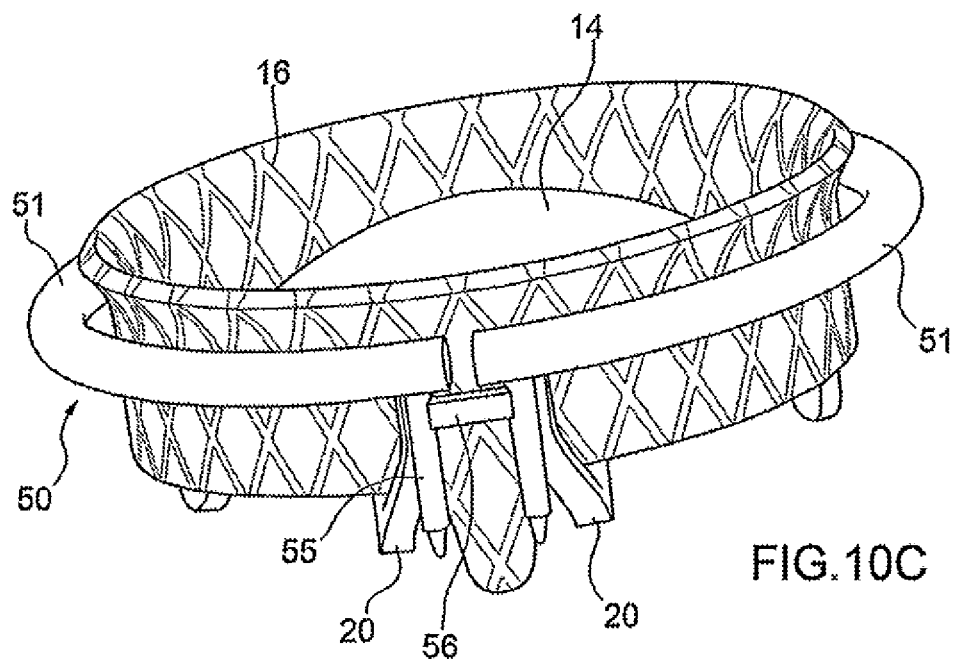

FIG. 10C shows the segments 51 of the containment portion 50 reconnected to the central element 16 of the prosthetic structure through the pin-hole couplings created with the connecting elements 20. It can be seen how, in the embodiment described in FIG. 10, at the end of the process to reconstitute the unity of the prosthetic structure, the containment portion 50 is continuous on all of the periphery of the device and non-extendable longitudinally owing to the presence of short transverse structures 56, an integral part of the connecting elements 20, which unite each couple of cylindrical cavities 55. Only after the unity of the prosthetic structure has been reconstituted, as shown in FIG. 10C, is it possible to proceed with the final positioning of the valvular prosthesis and its implantation. Only in the original configuration, in fact, is it possible at the same time to carry out the correct positioning of the prosthesis with respect to the native valve, the optimum mutual positioning of the containment portion 50 and the central support element 16, ensuring the perfect tightness of the prosthesis to counter flow, the effective anchoring of the prosthesis to the implantation site, with the stability contributed by the connecting elements, as described previously.

It is clear that the pin-hole connecting mechanism, as described in FIG. 10A-FIG. 10C is given purely by way of example, without any intention of limiting the general nature of the invention. Various solutions for creating a reversible coupling between the segments of the containing element and the connecting elements are known in the prior art and are usable in single embodiments of the invention described here.

FIG. 11A to FIG. 11G illustrate, purely by way of example, an implantation procedure of the embodiment of the implantable prosthetic device described in FIG. 10. The sequence illustrated in FIG. 11 hypothesises a minimally invasive surgical procedure intended to replace the mitral valve, operated on without removing the native valve. Access to the implantation site is through the left atrium with an anterograde approach to the mitral valve, according to the normal practice followed in surgical procedures. It is assumed that the left ventricle is empty and therefore accessible either directly or through endoscopic techniques known at the state of the art, but not necessarily with arrested heart. The technology and philosophy of the treatment remain substantially valid and usable even using retrograde access, for example apical, and a transcatheteral-type procedure, based on interventional techniques which allow the execution of the procedure even with the heart closed and in complete absence of extracorporeal circulation.

To describe the implantation procedure, the same anatomical model of the left side of the heart already described in FIG. 2 is used.

Figure 11A:
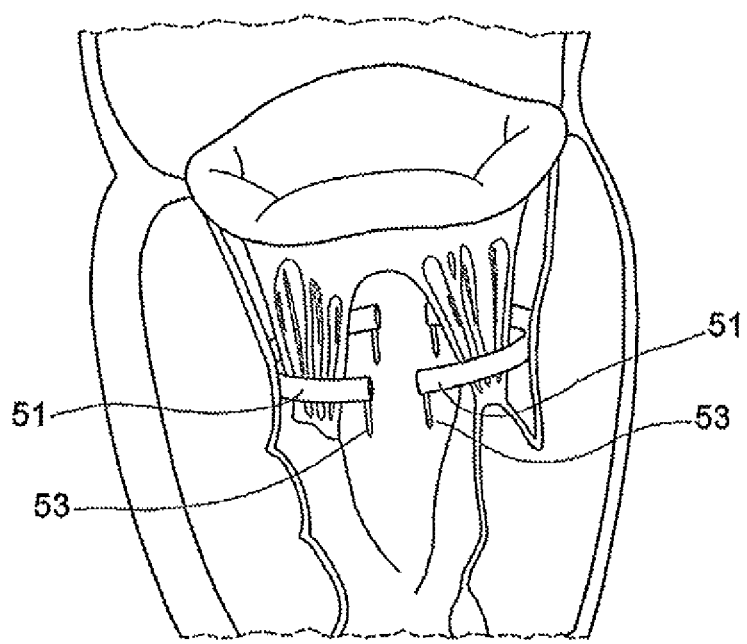
FIG. 11A to FIG. 11G show an example of an implantation procedure using a minimally invasive surgical procedure of the prosthetic device for the treatment of heart valves described in FIG. 10A to FIG. 10C, FIG. 12A and FIG. 12E show, according to different views, a general schematic representation of a prosthetic device for the treatment of heart valves, in accordance with an embodiment of the invention, characterised by being equipped with a mechanism for locking the containment portion to the valve portion of the prosthetic device, compatible with an implantation procedure based on transcatheteral techniques.

FIG. 11A shows the first step in the procedure, consisting in the positioning, inside the ventricular cavity, of two semi-arched segments which form the subcomponents 51 of the containment portion 50 of the prosthetic structure. For what has been said about the procedure adopted here, the subcomponents 51 are introduced into the left ventricle through the mitral valve, with direct manipulation compatible with the surgical approach. Each of them is positioned on the back of a commissural region of the mitral valve, embracing the entire bundle of tendinous cords involving the corresponding half of the valve. The orientation of subcomponents 51 is such that the connecting pins 53 are directed towards the apex of the ventricle, that is distally to the operator. Surgical access makes it possible to have a direct view, possibly supported by endoscopic instrumentation, of the implantation site and in particular of the inside of the left ventricle. It is therefore possible to check accurately the positioning of the two subcomponents 51, for example as regards their arrangement outside the entire mitral subvalvular apparatus, before proceeding to the next phase.

Figure 11B:
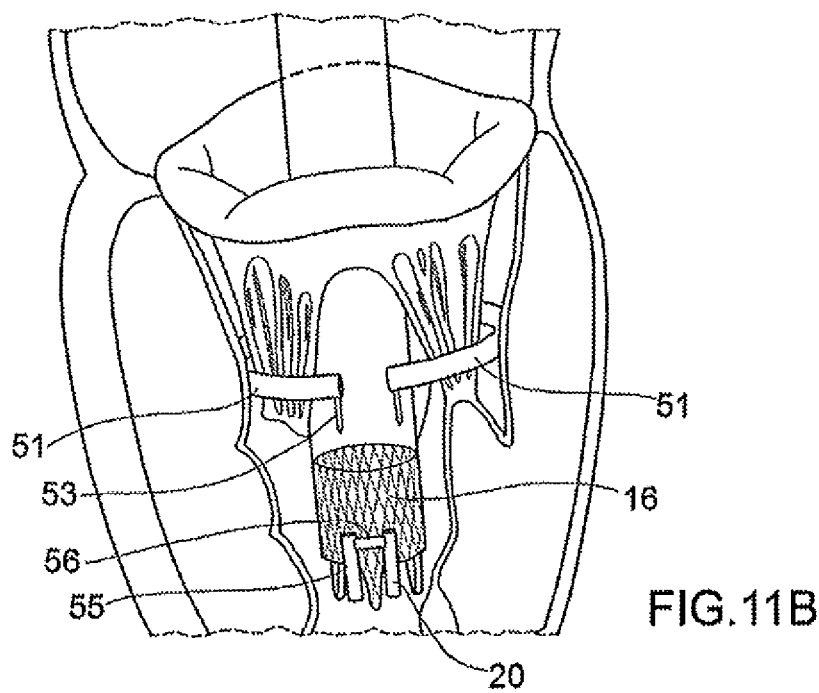

FIG. 11B shows the introduction into the ventricular cavity of the remaining portion of the prosthetic structure, with the central support portion 16 collapsed to its radial diameter of a lesser size and maintained in this configuration using a containing sheath of a release system. The connecting elements 20 can be left free outside the sheath of the release system, or they too can be compressed inside the sheath during the introduction operation into the ventricular cavity, in order to have an atraumatic introduction profile and a small profile, to then be selectively released once inside the ventricle. For simplicity of representation, FIG. 11B shows the free connecting elements 20, in a position at a distance from the subcomponents 51 of the containment portion.

Figure 11C:
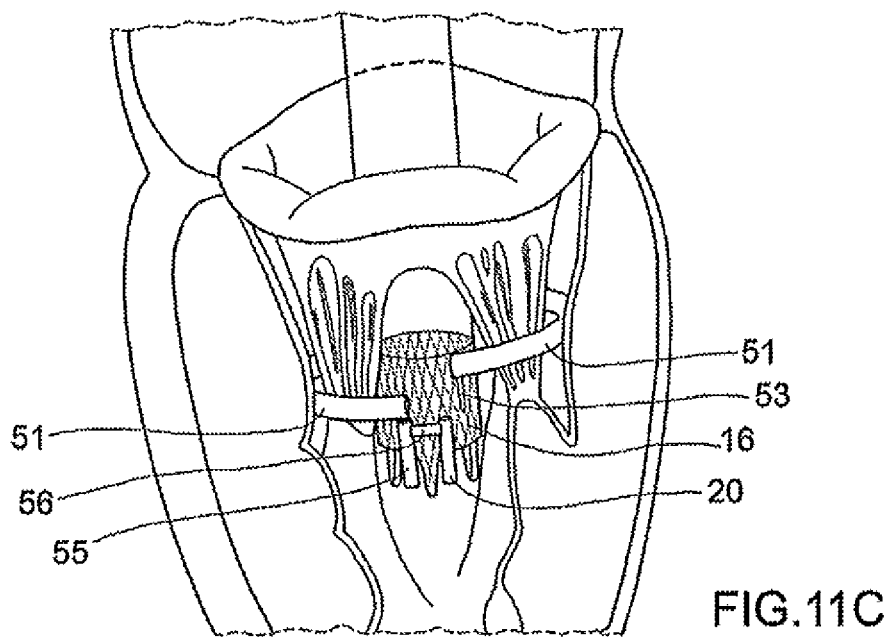

FIG. 11C shows a first subcomponent 51 of the containment portion 50 reconnected to the central support element 16 through the connecting elements 51, using the pin-hole couplings pre-arranged on both parts. This operation can easily be completed under direct or endoscopic view during an open-heart surgical procedure, while interventional techniques are required in the case of closed-heart transcatheteral procedures.

Figure 11D:
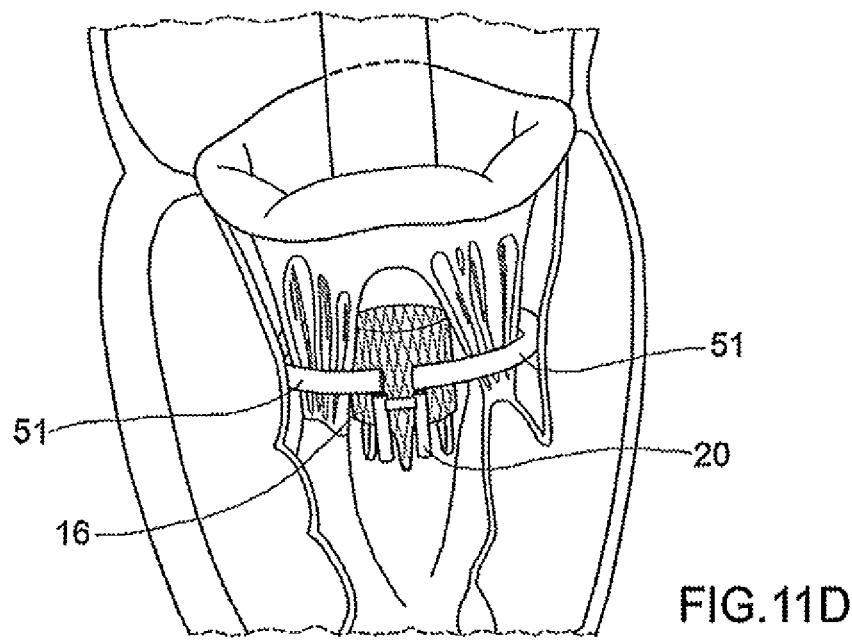

FIG. 11D shows the same operation carried out on the other subcomponent 51 of the containment portion. The unity of the prosthetic structure is therefore entirely reconstituted, and the prosthetic device is ready to be implanted. The mitral valve, including its subvalvular apparatus is entirely contained between the central support element 16, still in its collapsed configuration to a minimum radial size, and the annular containment portion 50, entirely deployed in the ventricular cavity outside the valve itself. Said portions of the prosthetic structure are connected and integrated between them through the connecting elements 20, in accordance with the principal dictated by the present invention and according to the embodiment illustrated in FIG. 1.

Figure 11E:
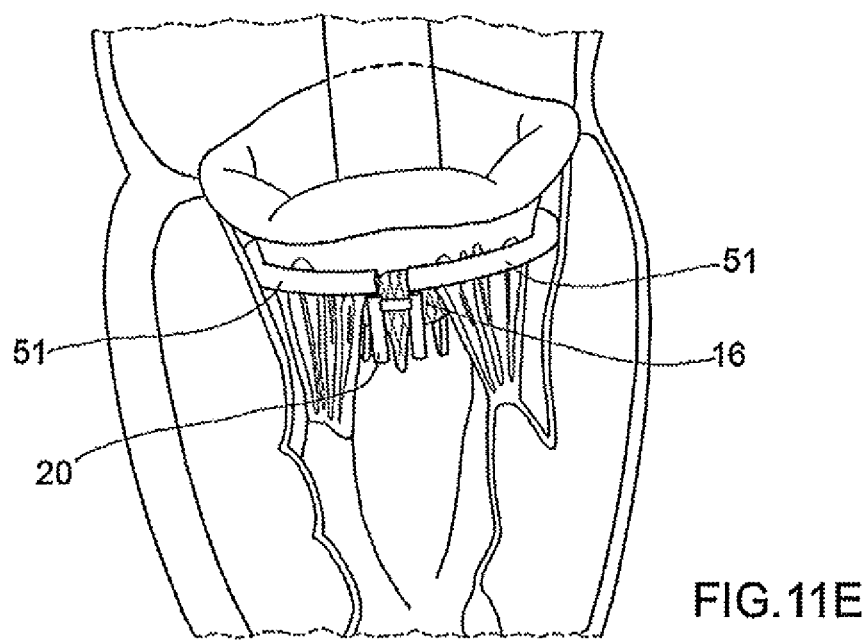
Figure 11F:
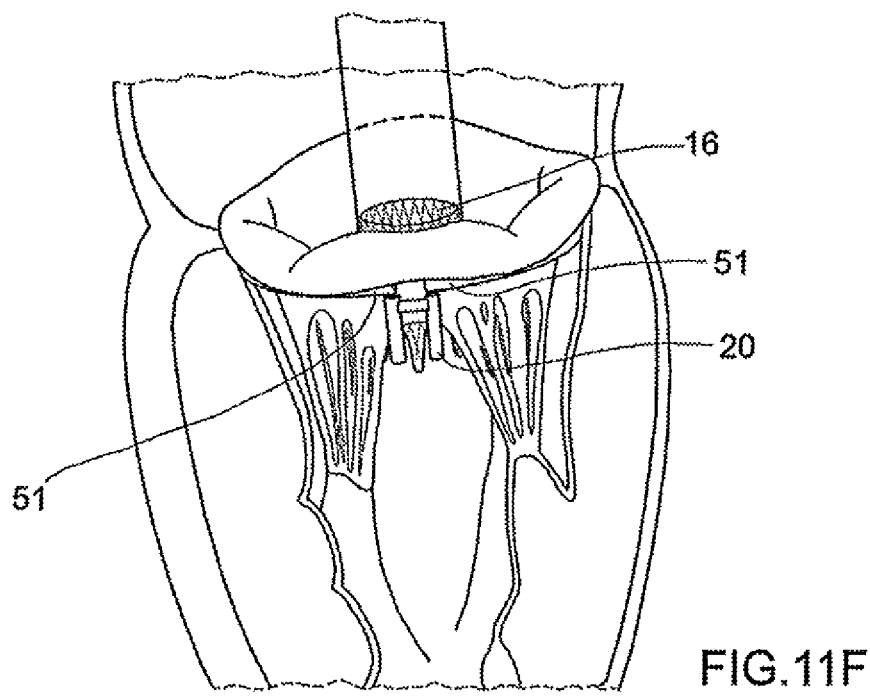

FIG. 11E and FIG. 11F show how, the unity of the prosthetic structure having been reconstituted, the repositioning of the central support element 16, obtained by the implanter through the release system, involves the automatic repositioning of the containment element 50 too. The release system is therefore shifted proximally, in such a way as to reach the correct implantation position. The correct implantation position is when the containment portion 50 is in contact with the ventricular aspect of the annulus of the mitral valve, allocated into the so-called subannular groove, while the central element 16 of the prosthetic device is, still in the collapsed configuration, astride the native valve. The configuration illustrated in FIG. 11F, immediately before final implantation, makes it possible to appreciate how the prosthetic device, conceptually described in FIG. 1, independently of the various embodiments of the invention, is a device able to position itself in the best way without particular skills being required of the operator. In fact, the structural unity existing between the containment portion 50 and the central support element 16 prevents the prosthesis being arranged in too distal a position (that is too deep into the ventricle) or too proximal a position (that is shifted too much towards the atrium) in relation to the ideal plane of the native annulus. It is in fact sufficient for the implanter to apply slight traction in a proximal direction on the release system to be certain that the containment element 50 is exactly in contact with the valvular annulus and that the correct release position has been reached. The impossibility of the containment portion 50 being able to migrate into the atrium, said portion being segregated on the ventricular side of the annulus of the same native mitral valve, does in fact prevent the traction exercised on the release system from generating too proximal a positioning of the prosthetic device.

Figure 11G:
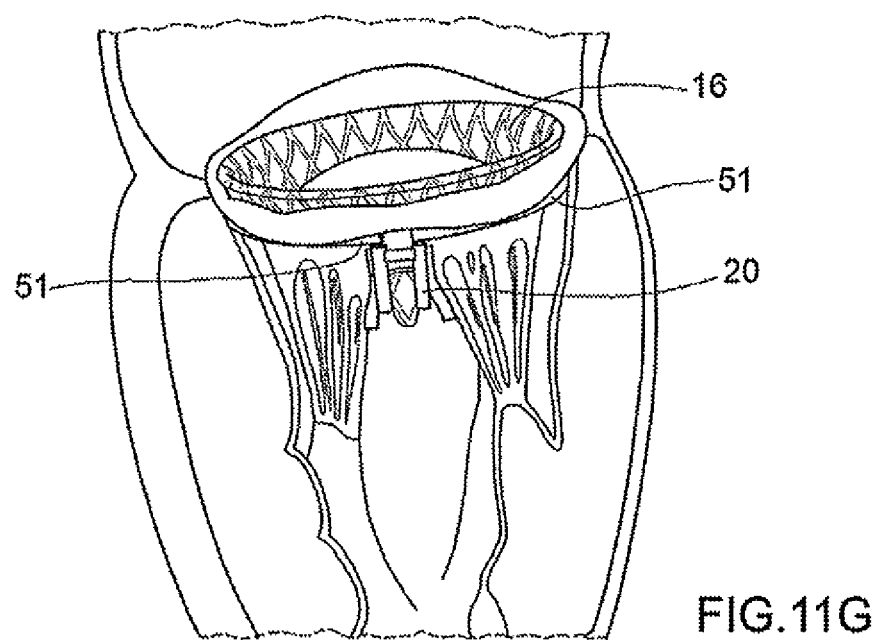

FIG. 11G shows the last phase of the implantation procedure, with the release of the central support element 16 and its expansion up to it reaching and coming into contact with the containment portion 50. The leaflets of the native mitral valve, entrapped between the two elements of the prosthetic structure, provide for and ensure stable anchoring of the prosthesis and effective tightness to the counterflow of the blood.

A different embodiment of the implantable prosthetic device fully compatible with the use of transcatheteral interventional procedures is illustrated in the figures from FIG. 12A to FIG. 12E.

Figure 12A:
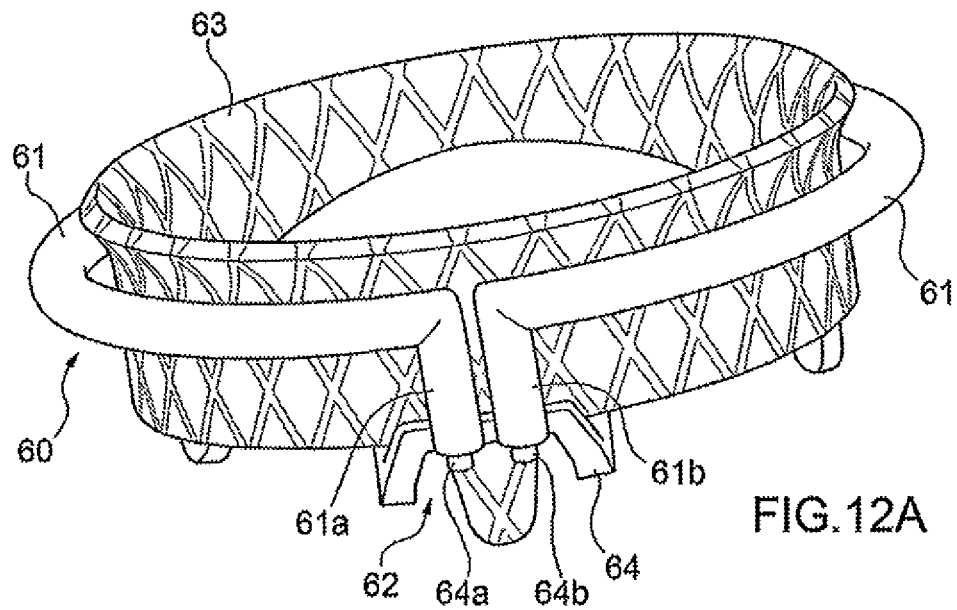
Figure 12B:
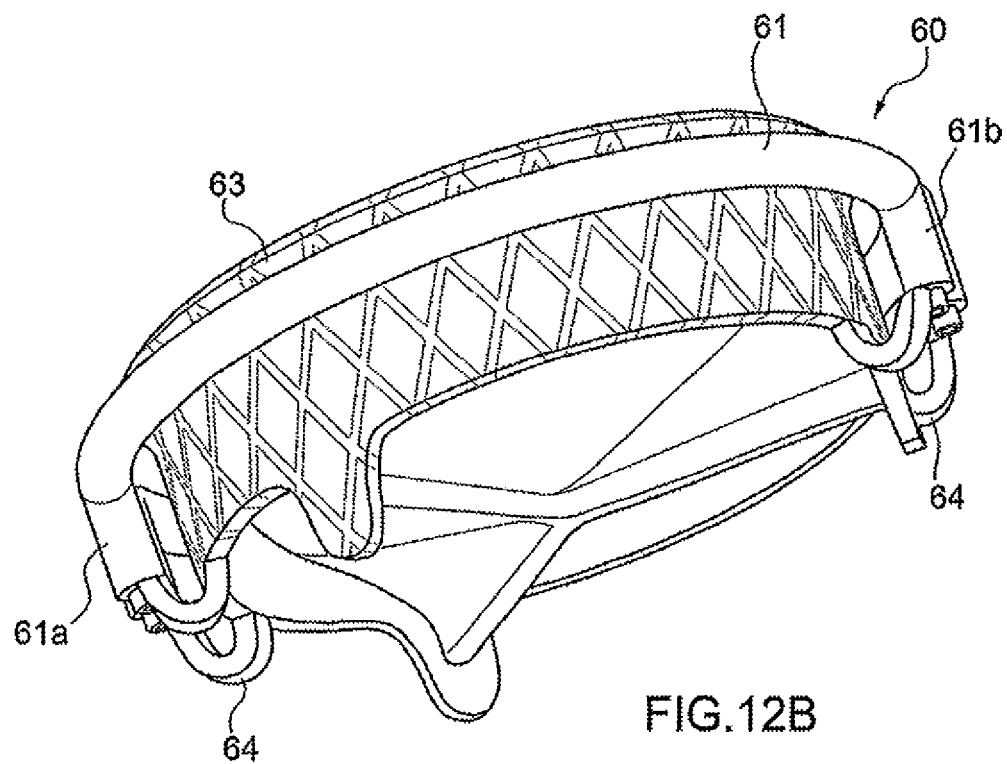

FIG. 12A and FIG. 12B, according to two different perspectives for a better understanding of the description, show the valvular prosthetic device in a particularly advantageous embodiment for implantation on an atrioventricular valve using transcatheteral techniques. In this case too, similarly to the previous embodiments, a containment portion 60 can, in its entirety, have any two-dimensional or three-dimensional form, according to the anatomy of the healthy or pathological atrioventricular valve, just as it can be subdivided into two or more segments or separate sub-components 61. Each sub-component 61 is temporarily separable, using a reversible locking mechanism 62, from those connecting elements 64 to which, on the other hand, it is coupled in the final configuration of the implant.

Figure 12C:
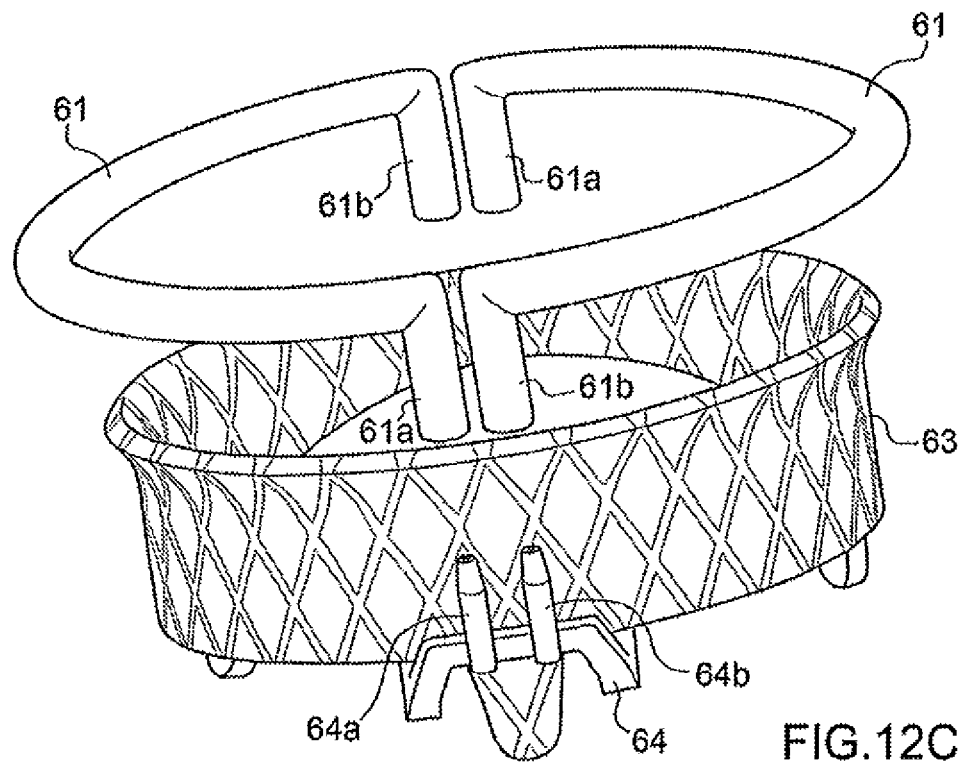

FIG. 12C shows the prosthetic device with the sub-components 61 making up the containment portion 60 separated from the central portion 63, in order to make the structure of the reversible locking mechanism 62 of the portions of the prosthesis more visible.

Figure 12D:
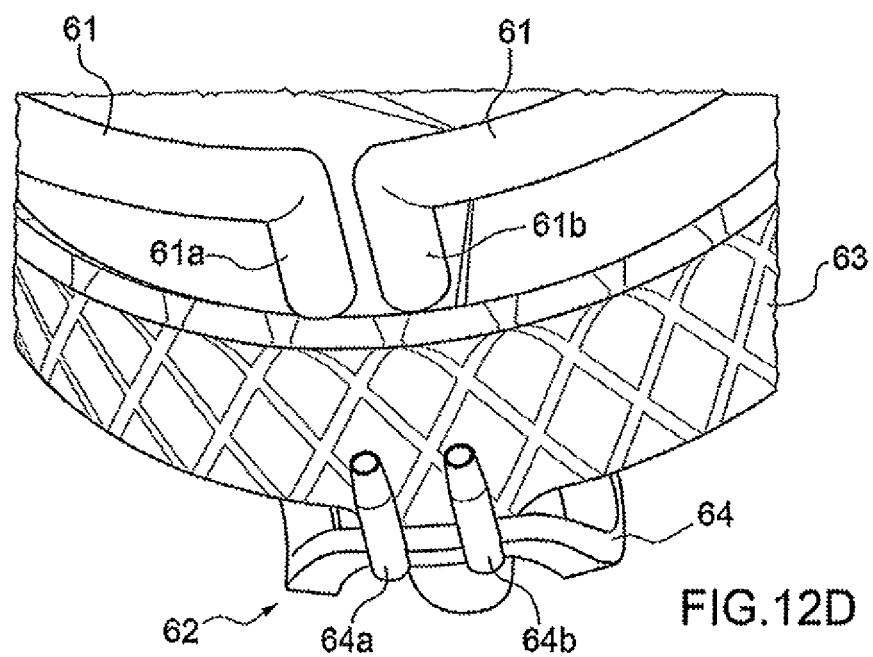
Figure 12E:
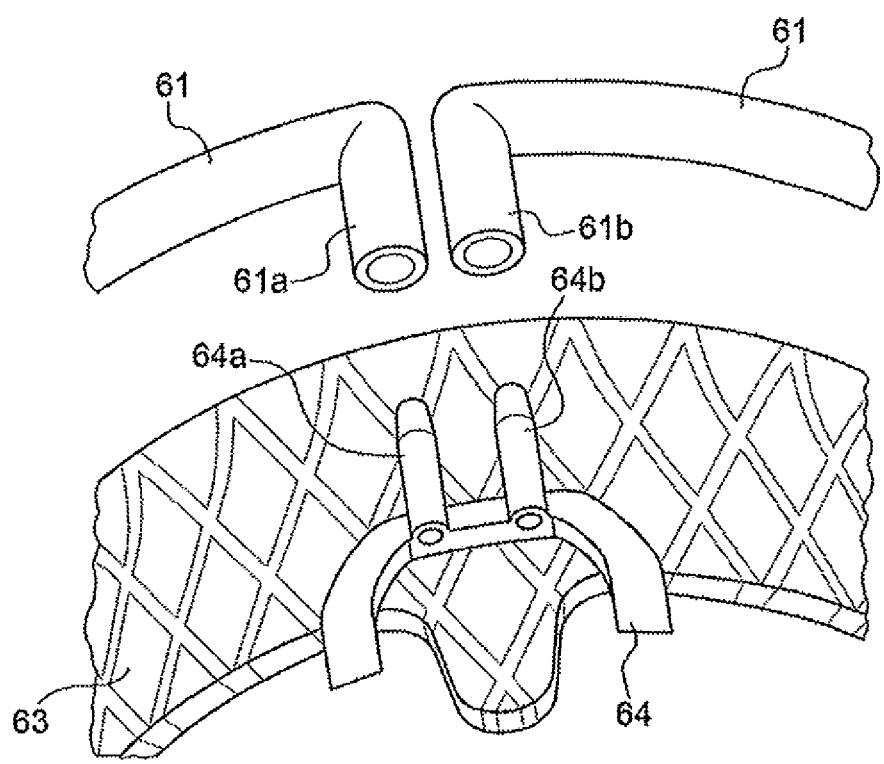

FIGS. 12D and 12E illustrate an enlarged detail of the locking mechanism 62.

In the solution described here, without this limiting the general nature of the invention, the connecting elements 64, which are integral to the central portion 63 and protrude externally at its periphery, are each equipped with a couple of hollow pins 64a, 64b, which are parallel and adequately spaced apart and are substantially aligned with the axis of the prosthetic device itself. The number of connecting elements 64 is equivalent to the number of sub-components 61 in which the containment portion 60 of the prosthesis is subdivided in such a way as to allow the continuity of the containment portion 60 itself to be reconstituted by using the connecting elements 64. As shown in FIG. 12D, each pin 64a, 64b of the same sub-component 61 is hollow and therefore allows a guidewire to pass freely inside it, as will be more clearly described below. Similarly, each end 61a, 61b of each sub-component 61 of the containment portion 60 also consists of a, preferably but not restricted to, substantially cylindrical hollow structure, as shown in FIG. 12E, suitable not only for the free passage of a guidewire, but also having dimensions such as to allow stable coupling with the corresponding pin 64a, 64b present on the connecting element 64. The hollow ends 61a, 61b of each sub-component 61 of the containment portion 64 are orientated substantially perpendicularly to a principal plane of the sub-component itself. In this way, the containment portion 60, in its entirety, is parallel to the annular plane of the native valve once the structural unity of the valvular prosthetic device has been reconstituted.

Both the cylindrical cavities present at the ends 61a, 61b of the sub-components 61 of the containment portion 60 and the pins 64a, 64b present on the connecting elements 64 can be provided with lamellae or teeth or other surface discontinuities suitable for increasing the friction in the pin-hole coupling, improving the stability of the mutual connection.

Finally, the entire structure of each sub-component 61 of the containment portion 60 can provide a passage for a guidewire 65', 65" along all or at least most of its length. In this way it will be easier to position the sub-component 61 inside the ventricular cavity on the back of the native valve leaflets. It is, in fact, enough to arrange the guidewire 65', 65", using well-known interventional techniques currently used in clinical use, along the path which identifies the desired positioning of the sub-component 61 and introduce said sub-component so that it runs along the guidewire 65', 65" itself.

FIG. 13A to FIG. 13E show a possible embodiment of sub-component 61, in which the containment portion 60 is sub-divided, which is particularly suitable for an implantation procedure carried out by means of transcatheteral techniques.

Figure 13A:
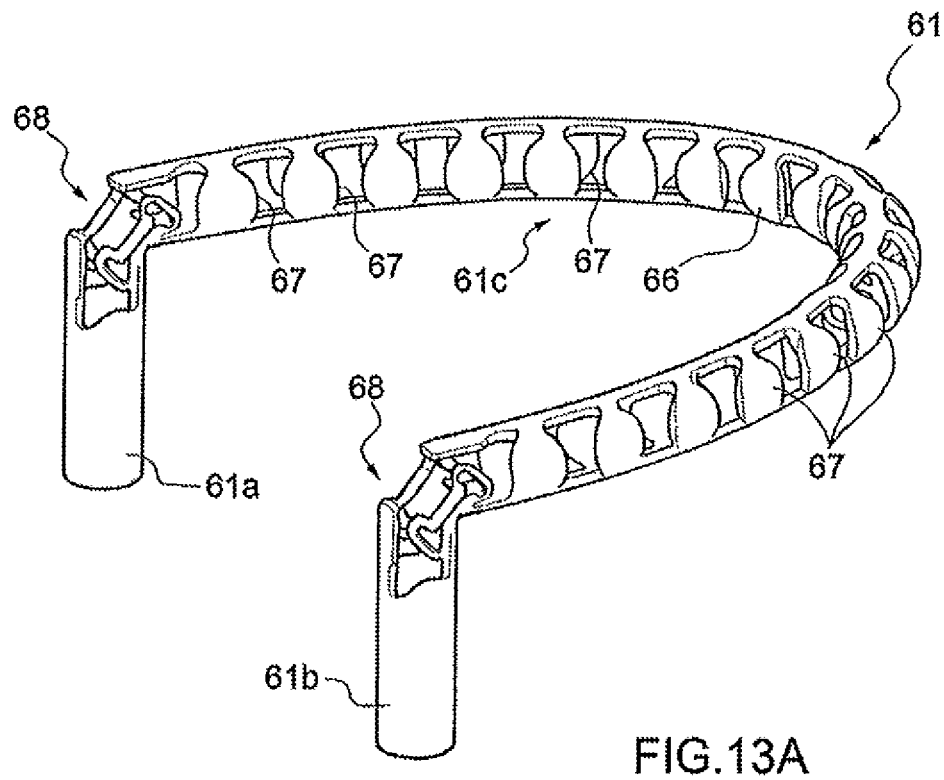
FIG. 13A to FIG. 13E show an example of an embodiment of the segments in which the containment portion is subdivided, according to an embodiment of the invention, comprising sections with a unidirectional elastic joint which allow the segments of the containment portion to recover a straight configuration taking up little radial space, particularly suitable for use in transcatheteral implantation procedures.

FIG. 13A shows, for representational simplicity, only the structural part of the sub-components 61 comprising the containment portion 60 of the prosthetic device. As has already been described previously, the structural part is obtained substantially from a tubular element 66 on the wall of which openings 67 have been made and are appropriately sized and positioned and suitable for providing the structure with the desired elastic behaviour, which can be anisotropic and variable from section to section, according to the position along the path of the sub-component 61. Then the structure of the sub-component 61 is shaped as shown schematically in FIG. 13A: the central section 61c is curved consistently with the geometry chosen for the containment portion 60, while the ends 61a, 61b are substantially deflected at right angle in respect of the central section 61c of the sub-component 61. The final shape of the sub-component 61, such as the shape shown in FIG. 13A, can be assigned to it in the production phase using suitable heat treatments applied to the piece held inside a mould.

In FIG. 13A, the two ends 61a, 61b of a preferably cylindrical shape, are clearly identifiable, substantially deflected at right angle in respect of the main plane of the structure of the central section 61c. These ends 61a, 61b comprise the elements of the sub-component 61 that form part of the connection mechanism to the central portion 63 of the prosthetic device. These ends 61a, 61b are connected to the central section 61c of the structure of the sub-component 61 through a transition zone 68 which acts as a unidirectional joint, allowing in one way the realignment of the ends on the same plane of the remaining portion of the sub-component 61, but, in the opposite direction, preventing a major deflection of 90° between the main plane of the sub-component 61 and the axis of the prosthetic device, once the sub-component 61 has been connected to the central portion 63 of the prosthetic device. This functional requirement avoids the risk of a deflection of the sub-components 61 of the containment portion 60 towards the inside of the ventricular chamber. In this way both the continuity of the contact of the containment portion 60 on the annulus of the native valve, and the correct mutual alignment between the containment portion 60 and the central portion 63 are guaranteed at the time of the final release of the prosthetic device.

Figure 13B:
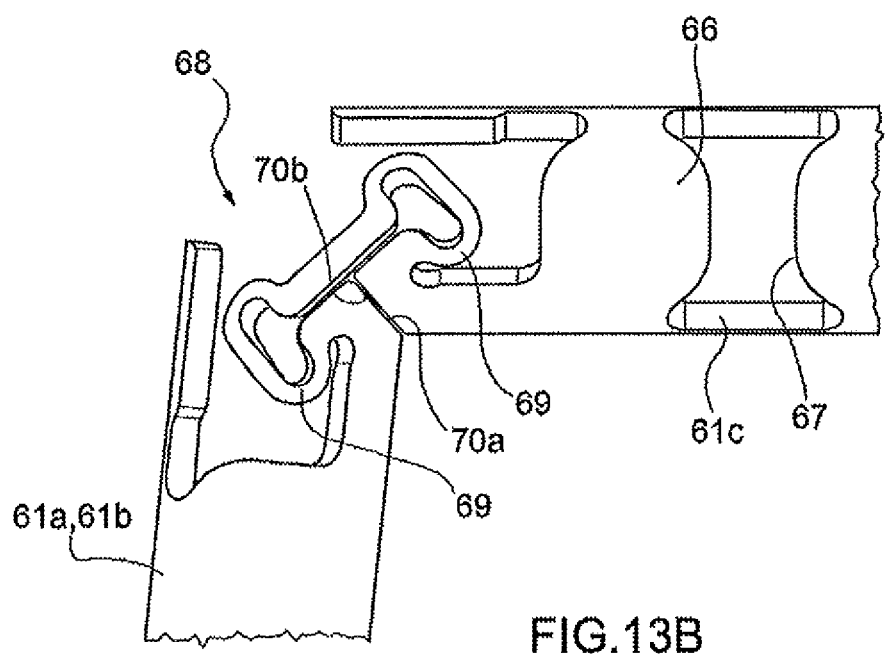
Figure 13C:
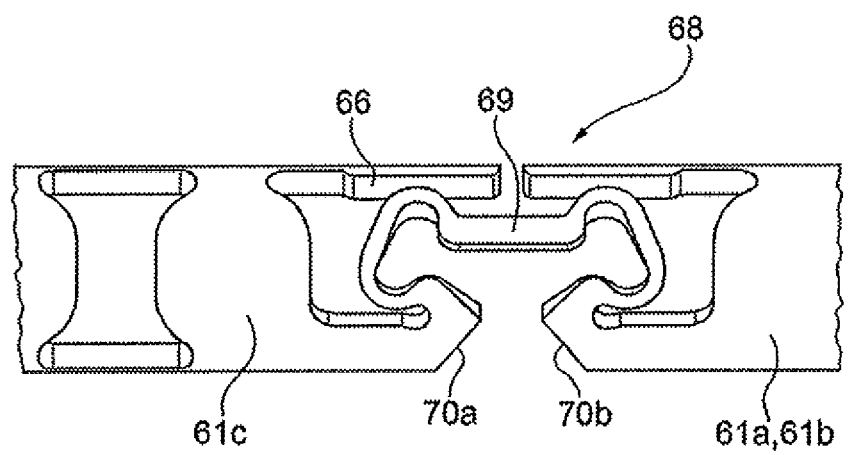

FIG. 13B and FIG. 13C illustrate by way of example, without limiting the general nature of the invention in doing so, an embodiment of said unilateral joint 68. In it, the end 61a, 61b of the sub-component 61 is connected to the rest of the structure 61c by a couple of coils 69, created directly in the wall of the tubular body 66, shaped in such a way as to act as a angular spring. This solution is compatible with the working processes of the sub-component 61 described previously.

In greater detail, FIG. 13B shows the bent, that is operational, configuration of the joint section 68. In order to create an angular end-stop, the lower surfaces 70a, 70b of the two sections of the tubular body adjacent to the joint 68 are cut at an angle in such a way that in the configuration deflected to 90° they come into contact with each other and at the same time the elastic coil 69 is closed as a package. The two aspects combined prevent the further deflection of the end 61a, 61b compared with the central section 61c of the structure of the sub-component 61. FIG. 13C shows the straightened configuration of the joint section 68. The surfaces of the two sections 70a, 70b previously in contact are separated, and the joining elastic coils 69 are open. The geometry of the elastic coil 69 is such that the deformation is distributed in a substantially uniform manner, avoiding concentrations of stress in the material.

Figure 13D:
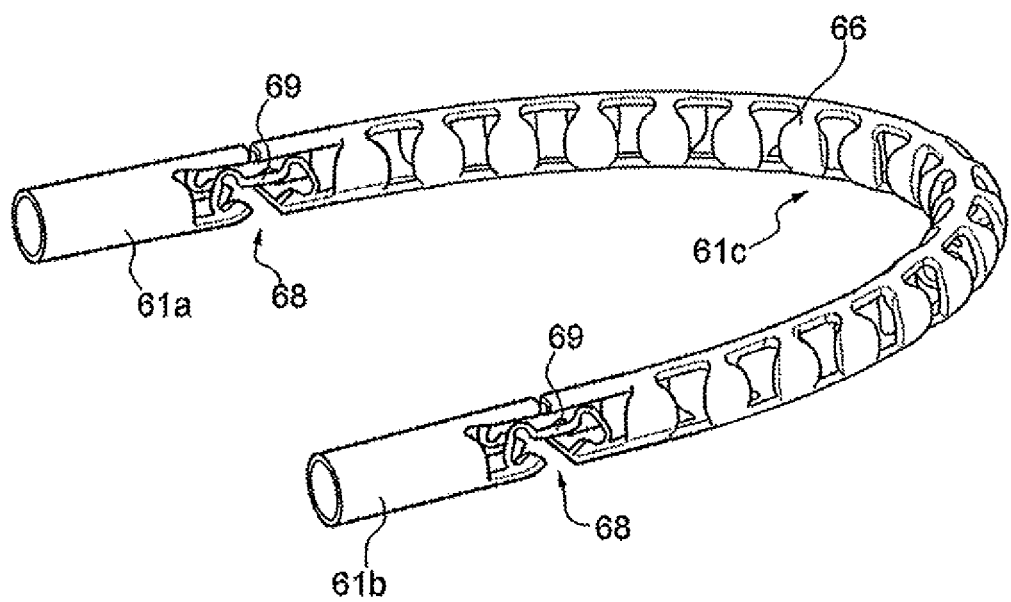
Figure 13E:
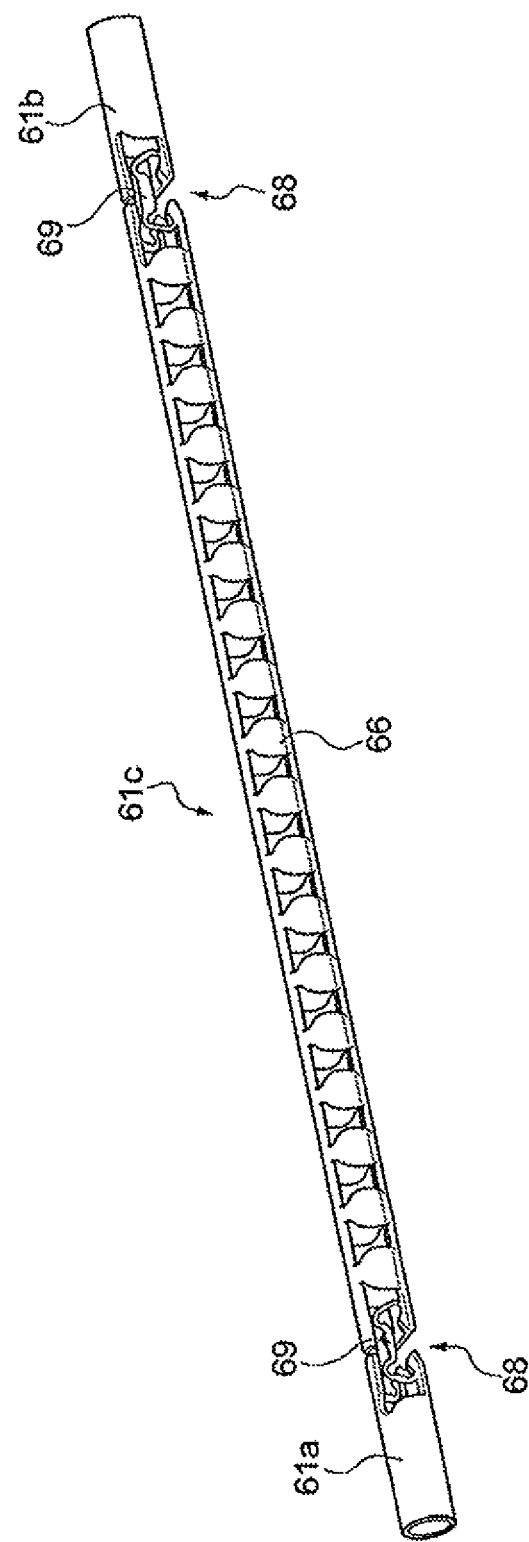

FIG. 13D and FIG. 13E show how the combined effect of the mesh design of the structure 66 and of the elastic joint 68 introduced near the ends 61a, 61b allows the sub-component to assume a substantially straight shape, particularly suitable for its implantation using transcatheteral techniques. In particular, FIG. 13D shows the straightening of the ends 61a, 61b, made possible by the elastic joint 68, a possible embodiment of which is illustrated in FIG. 13B and FIG. 13C. FIG. 13E shows the straight configuration of the sub-component 61 made possible by the mesh design of the central section 61c of sub-component 61.

It is clear to anyone who is an expert in the sector that other alternative embodiments of the invention to that described in FIG. 13 can provide either a different design of the elastic coils 69, or solutions which have the central section 61c and the ends 61a, 61b of the structure created as separate parts, joined together by elastic joints, in the form of additional components made of metallic or polymeric material.

Purely by way of example, without limiting the general nature of the invention in any way, FIG. 14A to FIG. 14E illustrate a possible transcatheteral implantation procedure of the embodiment of the implantable prosthetic device described in FIG. 12, including the connection of the containment portion 60 to the central portion of the prosthesis 63 in ways compatible with a totally transcatheteral interventional procedure. To make the drawings clearer, in this group of figures the depiction of the native atrioventricular valve is omitted. Furthermore the case is shown of a prosthesis having the containment portion subdivided into two segments or sub-components 61. Obviously a wholly analogous procedure can also be carried out in the case in which the containment portion is sub-divided into a greater number of sub-components.

Figure 14A:
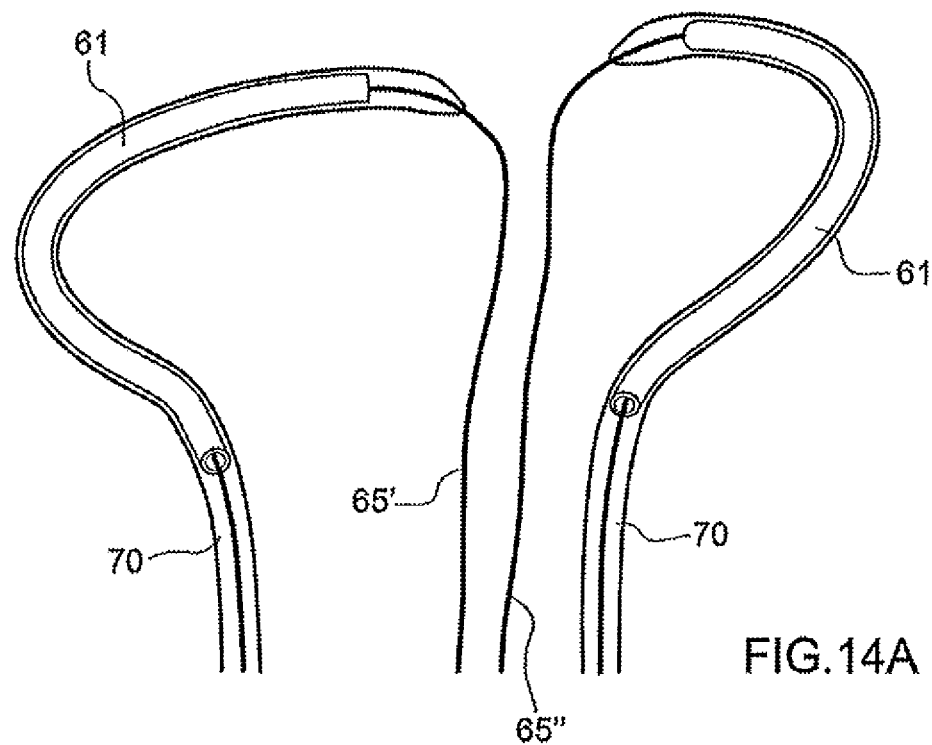
FIG. 14A to FIG. 14G show an example of an implantation procedure based on transcatheteral techniques of the prosthetic device for the treatment of heart valves having the connecting mechanism illustrated in FIG. 12A to FIG. 12E and the segments of the containment portion according to that illustrated in FIG. 13A to FIG. 13E.

FIG. 14A shows the positioning, in outline, using catheters 70 with a low radial profile, of the sub-components 61 of the containment portion 60 of the prosthesis on the back of the leaflets of the native atrioventricular valve. To facilitate and guarantee a good outcome for this operation, guidewires 65', 65" are used, one for each sub-component 61, which have been arranged beforehand in line with the final position required for the sub-components 61 themselves. It is in fact a well-known technique in the current state of the art of cardiac interventional procedures of how to navigate a guidewire inside the chambers of the heart. Each sub-component 61, previously straightened according to that shown in FIG. 13E and mounted inside a catheter 70 with a low profile, is therefore guided by the corresponding guidewire 65', 65" until it reaches the final desired position. This operation is made possible by the presence of a passage for a wire inside the structure 66 of the sub-component 61.

Figure 14B:
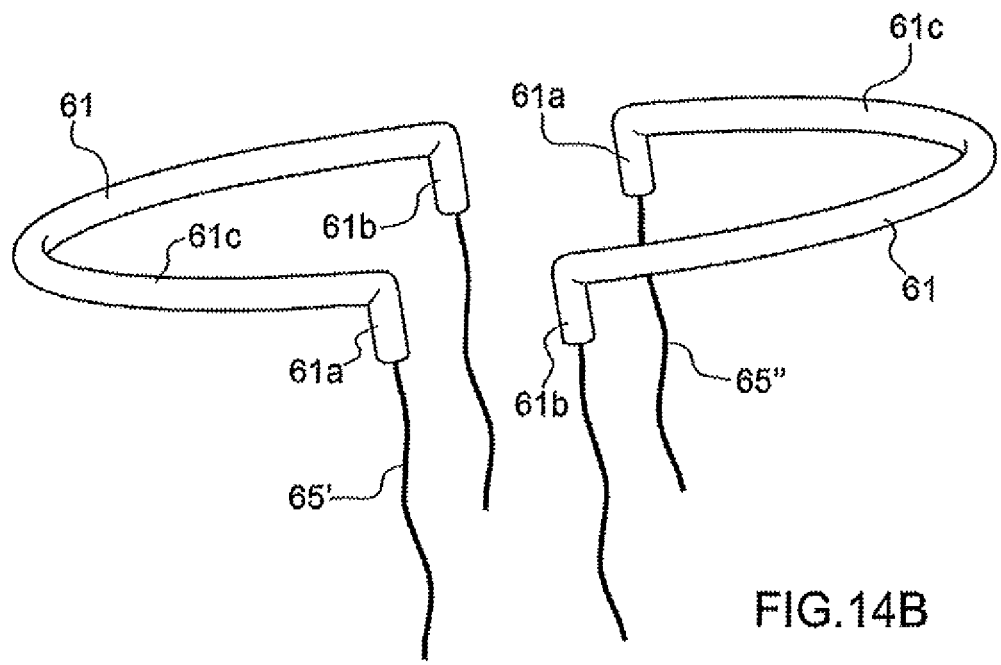

FIG. 14B shows how, once the sub-component 61 has been taken to its optimum position for implantation, the catheter 70, which has conveyed it, will be removed, nevertheless leaving the guidewire 65', 65" in situ, that is through the structure 66 of the sub-component 61 and with both ends accessible to the operator. Released from the catheter sheath 70, the sub-component 61 regains its original configuration having the curvature of the central section 61c itself and its ends 61a, 61b deflected in respect of the plane of the central section 61c.

Figure 14C:
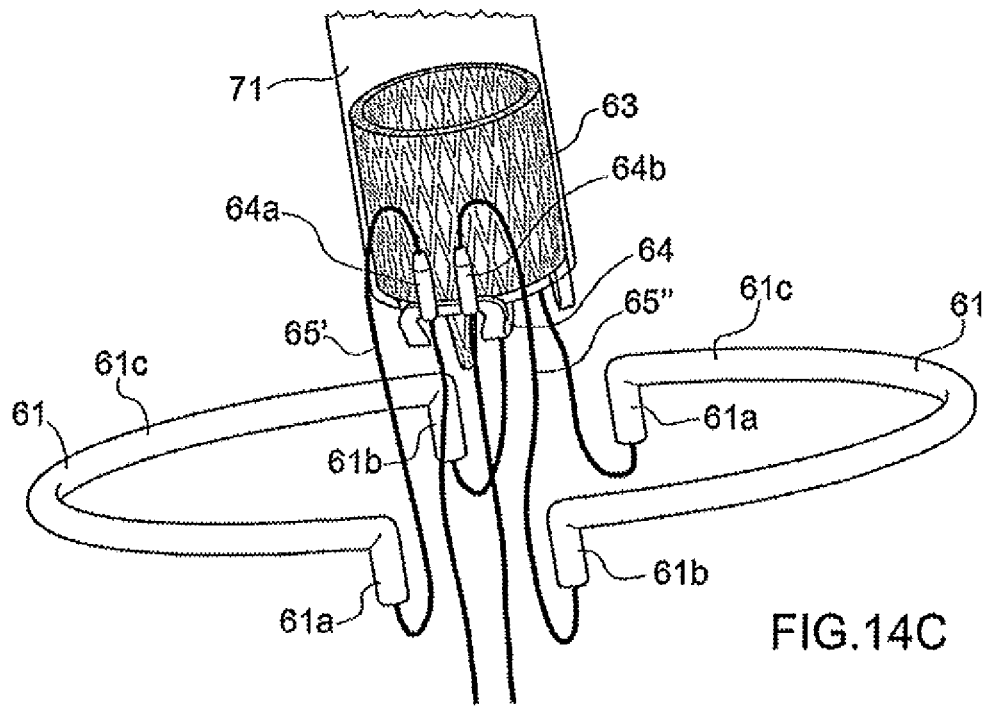

FIG. 14C shows the central portion 63 of the prosthesis, collapsed to its smaller radial diameter, being maintained in this configuration inside a release system 71, with the free ends of the guidewires 65', 65" inserted in the passages for the wires present inside each pin 64a, 64b of each sub-component 61 of the connecting mechanism 64. In this way each guidewire 65', 65" connects a couple of pins 64a, 64b which are integral to the central body 63 of the prosthesis and positioned on two separate and adjacent connecting elements 64, to the two ends 61a, 61b of the corresponding sub-component 61 of the containment portion 60.

Figure 14D:
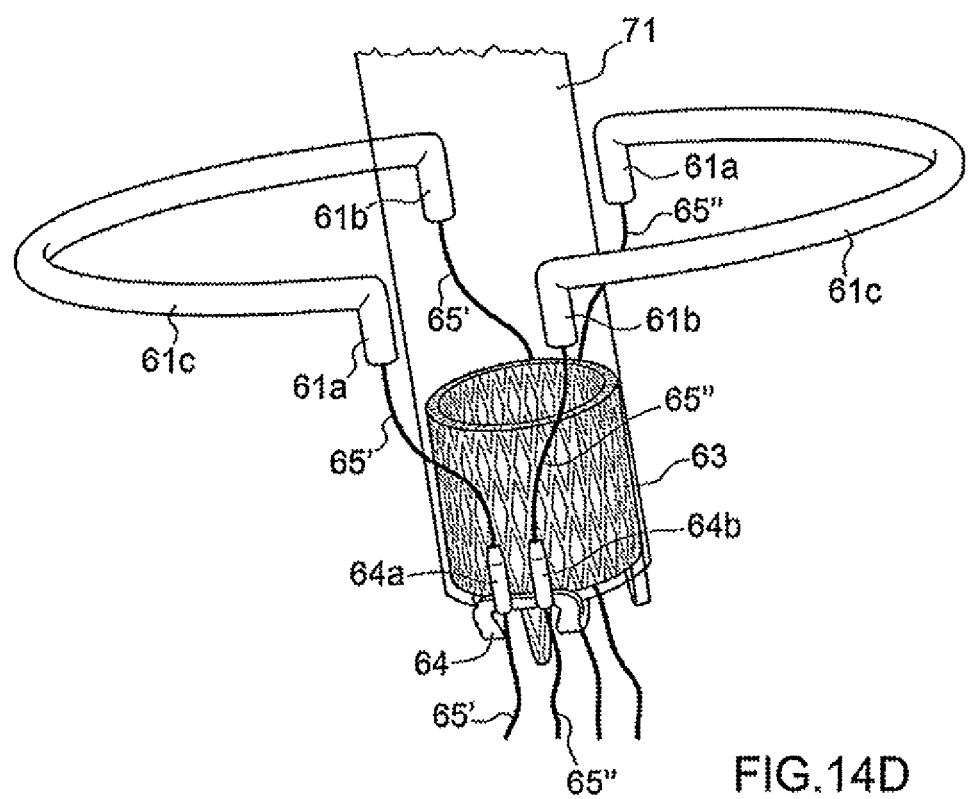

FIG. 14D shows the central portion 63 of the prosthesis, still in the collapsed configuration inside the release system 71, introduced inside the cardiac cavity in order to reach the implantation position.

Figure 14E:
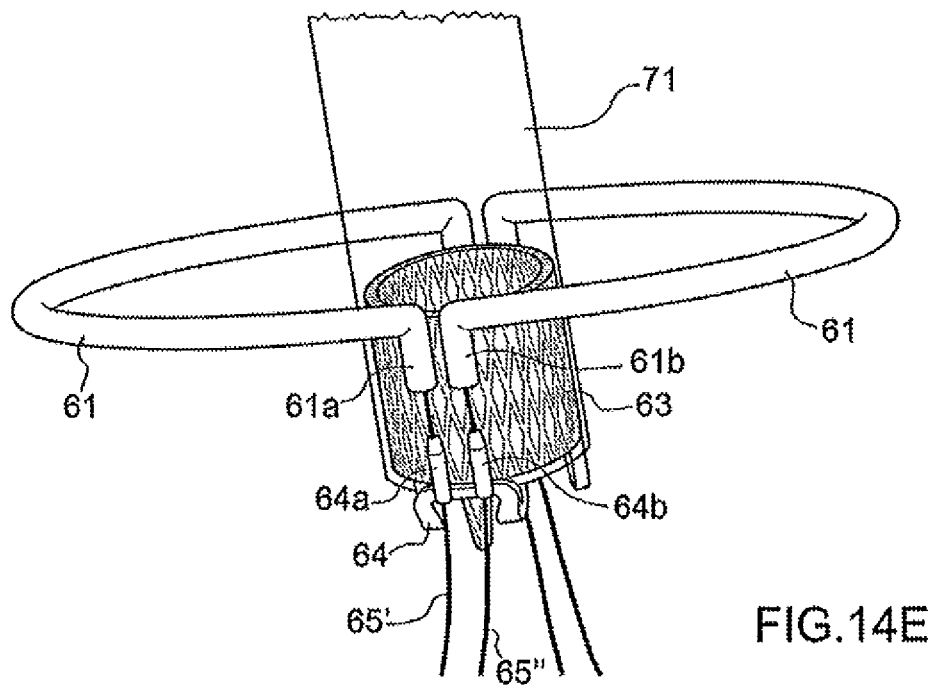

FIG. 14E shows how the tensioning of the guidewires 65', 65" brings the ends 61a, 61b of the sub-components 61 of the containment portion 60 together and aligns them with the corresponding pins 64a, 64b which are integral to the connecting elements 64.

Figure 14F:
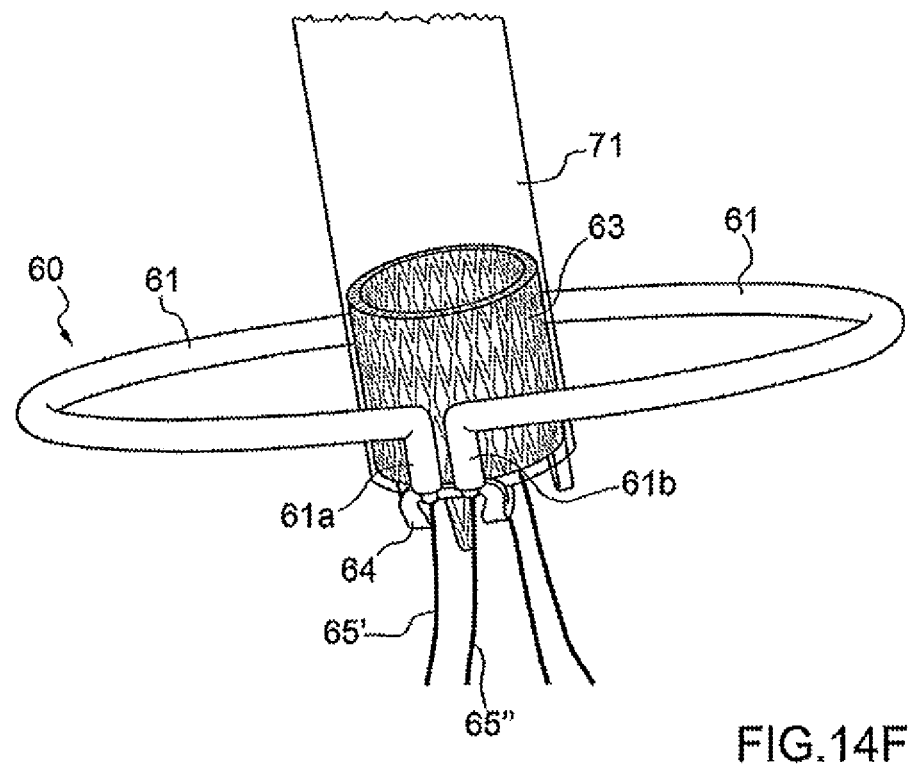

FIG. 14F shows how the further tensioning of the guidewires 65', 65" works the mechanical coupling between the ends 61a, 61b of the sub-components 61 of the containment portion 60 and the pins 64a, 64b which are integral to the connecting elements 64. In this configuration, both the structural continuity of the containment portion 60 and the unicity of the prosthetic device are reconstituted.

Figure 14G:
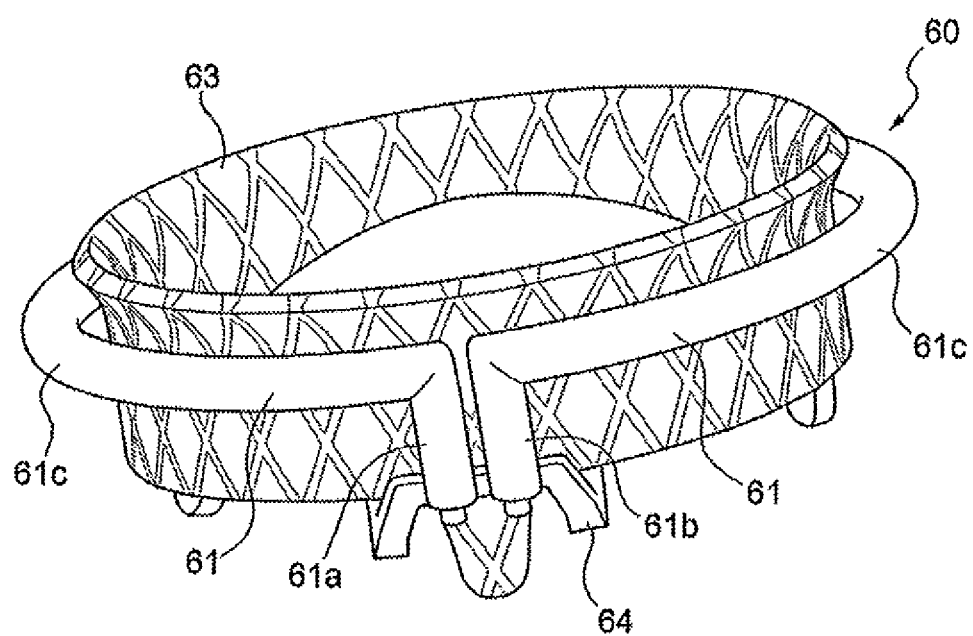

FIG. 14G finally shows the release of the central portion 63 and its expansion up to where it approaches and comes into contact with the containment portion 60. This being the final phase of the implantation procedure of the valvular prosthesis, both the guidewires 65', 65" and the release system 71 of the central portion 63 of the prosthesis can be removed from the cardiac chambers.

Naturally, without prejudice to the principle of the invention, the embodiments and the features thereof can vary considerably from that described and shown, without this departing from the scope of the present invention.

The invention claimed is:

1. Prosthetic device for a heart valve, comprising:
a valve portion with prosthetic leaflets capable of reproducing a function of valve leaflets of a native heart valve, expandable from a collapsed configuration for implantation to a working expanded configuration;
a containment portion which surrounds the valve portion to contain and restrain expansion of the valve portion in the working expanded configuration; and
a connecting portion which connects the valve portion to the containment portion through at least one connecting element;
the valve portion exerts an outward radial force necessary to guarantee effective anchorage of the prosthetic device, the outward radial force being exerted on the containment portion, and the containment portion prevents the outward radial force from being transferred to surrounding anatomical structure when the valve portion is in the working expanded configuration.

2. The prosthetic device according to claim 1, wherein the valve portion comprises a support element intended to support all the prosthetic leaflets, the connecting elements of the connecting portion comprising flexible elements for physical connection and structural unity between the support element and the containment portion.

3. The prosthetic device according to claim 1, wherein the containment portion comprises a plurality of separate segments, each of the separate segments comprising a connector for allowing the separate segments to form the containment portion into an annular continuity.

4. The prosthetic device according to claim 3, wherein at least one of the segments is temporarily separable from the valve portion.

5. The prosthetic device according to claim 1, wherein at least part of the containment portion is covered by tissue of a biological or artificial material or with polymer material, or a combination thereof.

6. The prosthetic device according to claim 1, wherein the containment portion includes a first part of a locking mechanism and further includes a second part of a locking mechanism, wherein the first part of the locking mechanism and the second part of the locking mechanism are compatible with a catheter, in which the containment portion is subdivided into sub-components to allow the containment portion to be positioned on a back of the valve leaflets of the native heart valve, the first part of the locking mechanism comprises at least one structure of the containment portion that is aligned and coupled to at least one structure of the valve portion using at least one guidewire.

7. Prosthetic device for a heart valve, comprising:
a valve portion comprising a support element and prosthetic leaflets fixed to an interior of the support element, the prosthetic leaflets capable of reproducing a function of valve leaflets of a native heart valve, expandable from a collapsed configuration for implantation to a working expanded configuration;
a containment portion which surrounds the valve portion to contain and restrain expansion of the valve portion in the working expanded configuration; and
a connecting portion which connects the valve portion to the containment portion through at least one connecting element;
the prosthetic leaflets include free margins that contact each other when the valve portion is in the working expanded configuration;
the containment portion prevents the support element from exceeding a maximum diameter compatible with preservation of contact between the prosthetic leaflets; and
the support element exerts an outward radial force necessary to guarantee effective anchorage of the prosthetic device, the outward radial force being exerted on the containment portion, and the containment portion prevents the outward radial force from being transferred to surrounding anatomical structure when the valve portion is in the working expanded configuration.

8. The prosthetic device according to claim 7, wherein the containment portion comprises a plurality of separate segments, each of the separate segments comprising a connector for allowing the separate segments to form the containment portion into an annular continuity.

9. The prosthetic device according to claim 8, wherein at least one of the segments is temporarily separable from the valve portion.

10. The prosthetic device according to claim 7, wherein at least part of the containment portion is covered by tissue of a biological or artificial material or with polymer material, or a combination thereof.

11. The prosthetic device according to claim 7, wherein the containment portion includes a first part of a locking mechanism and further includes a second part of a locking mechanism, wherein the first part of the locking mechanism and the second part of the locking mechanism are compatible with a catheter, in which the containment portion is subdivided into sub-components to allow the containment portion to be positioned on a back of the valve leaflets of the native heart valve, the first part of the locking mechanism comprises at least one structure of the containment portion that is aligned and coupled to at least one structure of the valve portion using at least one guidewire.

12. Prosthetic device for a heart valve, comprising:
a valve portion comprising:
- a support element with a longitudinal axis and being radially collapsible and expandable with respect to the longitudinal axis, and
- prosthetic leaflets fixed to an interior of the support element, the prosthetic leaflets capable of reproducing a function of valve leaflets of a native heart valve;

the support element being expandable from a collapsed configuration where the support element has a first radial extent for implantation to an expanded configuration where the support element has a second radial extent, greater than the first radial extent, where the support element delimits a conduit for the passage of blood through the prosthetic device;

a containment portion which surrounds the valve portion and has a third radial extent to contain and restrain expansion of the valve portion in the expanded configuration; and a connecting portion connecting the valve portion to the containment portion through at least one connecting element;

wherein the support element is expandable from the first radial extent to the second radial extent while the containment portion is maintained at the third radial extent.

13. The prosthetic device according to claim 12, wherein the containment portion is a structure with a two-dimensional or three-dimensional geometry which is substantially annular when seen from above.

14. The prosthetic device according to claim 13, wherein the containment portion is assemblable from an open configuration, suitable for making possible for insertion of the containment portion on a back of the native valve leaflets, to a substantially annular closed configuration.

15. The prosthetic device according to claim 14, wherein the containment portion comprises a plurality of segments each comprising a connector for assembled reconstruction of an annular continuity of the containment portion.

16. The prosthetic device according to claim 15, wherein at least one of the segments is temporarily separable from the valve portion.

17. The prosthetic device according to claim 12, wherein at least part of the containment portion is covered by tissue of a biological or artificial material or with polymer material, or a combination thereof.

18. The prosthetic device according to claim 12, wherein the containment portion includes a first part of a locking mechanism and further includes a second part of a locking mechanism, wherein the first part of the locking mechanism and the second part of the locking mechanism are compatible with a catheter, in which the containment portion is subdivided into sub-components to allow the containment portion to be positioned on a back of the valve leaflets of the native heart valve, the first part of the locking mechanism comprises at least one structure of the containment portion that is aligned and coupled to at least one structure of the valve portion using at least one guidewire.

19. The prosthetic device according to claim 18, in which each of the at least one guidewire is connected to one of the at least one structure of the containment portion and to one of the at least one structure of the valve portion.

20. The prosthetic device according to claim 19, in which the at least one structure of the containment portion and the at least one structure of the valve portion comprise hollow portions suitable for allowing the guidewire to pass through.

21. The prosthetic device according to claim 18, in which the valve portion has, on a periphery thereof, hollow structures suitable for passage of the guidewire suitable for carrying out mechanical coupling with corresponding hollow structures present on the containment portion.

22. The prosthetic device according to claim 18, in which each sub-component of the containment portion has joint mechanisms which allow each sub-component to be deformed elastically until each sub-component assumes a configuration taking up reduced radial space with respect to the working expanded configuration.

23. A method for assembling the prosthetic device according to claim 18, comprising the steps of:
providing the valve portion in the collapsed configuration;
surrounding the valve portion with the containment portion; and
connecting the valve portion to the containment portion through the connecting elements.

24. The method for assembling the prosthetic device according to claim 23, where the containment portion is assemblable from an open configuration to a substantially annular closed configuration.

25. The method for assembling the prosthetic device according to claim 24, wherein the containment portion comprises a plurality of segments each comprising a connector for assembled reconstruction of annular continuity of the containment portion.

26. The prosthetic device according to claim 12, wherein at least one structure of the containment portion is aligned and coupled to at least one structure of the valve portion using at least one guidewire.

* * * * *